(12) United States Patent
Mullen et al.

(10) Patent No.: US 9,840,607 B2
(45) Date of Patent: Dec. 12, 2017

(54) POLYHYDROXY KETAL ESTER ADDUCTS, METHODS OF MANUFACTURE AND USES THEREOF

(71) Applicant: SEGETIS, INC., Golden Valley, MN (US)

(72) Inventors: Brian D. Mullen, Delano, MN (US); Marc D. Scholten, Saint Paul, MN (US); Cora M. Leibig, Maple Grove, MN (US); Matthew J. Tjosaas, Minneapolis, MN (US); Dorie J. Yontz, Bloomington, MN (US)

(73) Assignee: GFBIOCHEMICALS LIMITED, Valletta (MT)

( * ) Notice: Subject to any disclaimer, the term of this patent is extended or adjusted under 35 U.S.C. 154(b) by 0 days.

(21) Appl. No.: 14/943,764

(22) Filed: Nov. 17, 2015

(65) Prior Publication Data

US 2016/0068660 A1   Mar. 10, 2016

Related U.S. Application Data

(62) Division of application No. 13/294,854, filed on Nov. 11, 2011, now Pat. No. 9,187,598.

(60) Provisional application No. 61/412,699, filed on Nov. 11, 2010.

(51) Int. Cl.
| | | |
|---|---|---|
| C08K 5/1565 | (2006.01) |
| C07D 317/02 | (2006.01) |
| C07D 317/14 | (2006.01) |
| C07D 317/30 | (2006.01) |
| C08G 2/32 | (2006.01) |
| C08G 63/668 | (2006.01) |
| C08G 63/91 | (2006.01) |
| C08G 64/02 | (2006.01) |
| C08G 64/42 | (2006.01) |
| C08L 59/00 | (2006.01) |
| C09D 159/00 | (2006.01) |
| C09D 167/00 | (2006.01) |
| C08G 18/32 | (2006.01) |
| C08G 63/672 | (2006.01) |
| C08L 67/00 | (2006.01) |
| C08G 101/00 | (2006.01) |

(52) U.S. Cl.
CPC .......... *C08K 5/1565* (2013.01); *C07D 317/02* (2013.01); *C07D 317/14* (2013.01); *C07D 317/30* (2013.01); *C08G 2/32* (2013.01); *C08G 18/3218* (2013.01); *C08G 63/668* (2013.01); *C08G 63/672* (2013.01); *C08G 63/91* (2013.01); *C08G 64/0208* (2013.01); *C08G 64/42* (2013.01); *C08L 59/00* (2013.01); *C09D 159/00* (2013.01); *C09D 167/00* (2013.01); *C08G 2101/0025* (2013.01); *C08L 67/00* (2013.01); *Y02P 20/582* (2015.11); *Y10T 428/31507* (2015.04); *Y10T 428/31786* (2015.04)

(58) Field of Classification Search
CPC ... C07D 317/02; C07D 317/14; C07D 317/30
See application file for complete search history.

(56) References Cited

U.S. PATENT DOCUMENTS

| | | |
|---|---|---|
| 2,004,115 A | 6/1935 | Izard et al. |
| 2,008,720 A | 7/1935 | Lawson |
| 2,260,261 A | 10/1941 | Morey et al. |
| 2,556,135 A | 6/1954 | Croxall et al. |
| 2,838,467 A | 6/1958 | Dobay |
| 2,985,536 A | 5/1961 | Stein et al. |
| 3,041,313 A | 6/1962 | Lavin |
| 3,201,420 A | 8/1965 | Fuzesi et al. |
| 3,963,800 A | 6/1976 | Gipp et al. |
| 4,085,081 A | 4/1978 | Heckles et al. |
| 4,792,411 A | 12/1988 | Walsh |
| 5,095,098 A | 3/1992 | McLain et al. |
| 5,202,413 A | 4/1993 | Spinu |
| 5,552,513 A | 9/1996 | Bhatia |
| 5,565,545 A | 10/1996 | Kriesche et al. |
| 5,741,882 A | 4/1998 | Fujii et al. |
| 5,917,059 A | 6/1999 | Bruchmann et al. |
| 5,998,092 A | 12/1999 | McCulloch et al. |
| 6,528,025 B1 | 3/2003 | Boesch et al. |
| 6,806,392 B2 | 10/2004 | Boesch et al. |
| 8,053,468 B2 | 11/2011 | Selifonov |
| 8,507,718 B2 | 8/2013 | Mullen et al. |
| 8,575,367 B2 | 11/2013 | Selifonov et al. |
| 2003/0167681 A1 | 9/2003 | Puche |
| 2003/0204042 A1 | 10/2003 | Moethrath et al. |
| 2004/0024260 A1 | 2/2004 | Winkler et al. |

(Continued)

FOREIGN PATENT DOCUMENTS

| | | |
|---|---|---|
| DE | 1031512 | 6/1958 |
| FR | 1445013 | 7/1966 |

(Continued)

OTHER PUBLICATIONS

Bechtold, et al., "Perfectly Alternating Copolymer of Lactic Acid and Ethylene Oxide as a Plasticizing Agent for Polylactide," Macromolecules 34: 8641-8648 (2001).
Burch, et al., "Synthesis of Cyclic Oligoesters and Their Rapid Polymerization to High Molecular Weight," Macromolecules 33: 5053-5064 (2000).
Carey et al., "Advanced Organic Chemistry, Second Edition, Part B: Reactions and Synthesis", Plenum Press, NY (1983) pp. 539-552.
Carey, Mark A., et al., "Rapid Method for Measuring the Hydroxyl Content of Polyurethane Polyols" (published on the Internet at http://www.polyurethane.org/s_api/doc_paper.asp?CE)=::1044 &DID=4060, accessed on Dec. 29, 2011) 11 pages.

(Continued)

*Primary Examiner* — Melissa Rioja
(74) *Attorney, Agent, or Firm* — Cantor Colburn LLP

(57) ABSTRACT

Disclosed herein is a polyhydroxy ketal adduct obtained by the esterification of a hydrocarbon polyol by at least 1.5 equivalents of a ketocarboxy to produce an intermediate ketocarboxylic ester. The intermediate polyketocarboxylic ester is then ketalized to produce the polyhydroxyketal adduct, which can be used to provide a polymeric composition.

11 Claims, No Drawings

(56) References Cited

U.S. PATENT DOCUMENTS

| | | |
|---|---|---|
| 2006/0069230 A1 | 3/2006 | Papisov |
| 2008/0242721 A1 | 10/2008 | Selifonov |
| 2010/0048940 A1 | 2/2010 | Tulchinsky et al. |
| 2010/0216915 A1 | 8/2010 | Bloom |
| 2011/0021658 A1 | 1/2011 | Selifonov |
| 2012/0035376 A1 | 2/2012 | Mullen et al. |
| 2012/0118201 A1 | 5/2012 | Mullen et al. |
| 2012/0122745 A1 | 5/2012 | Mullen et al. |
| 2013/0053564 A1 | 2/2013 | Selifonov et al. |
| 2013/0310288 A1 | 11/2013 | Mullen et al. |

FOREIGN PATENT DOCUMENTS

| | | |
|---|---|---|
| JP | 28004327 A | 9/1953 |
| JP | 2002348451 A | 12/2002 |
| WO | 2005097723 A2 | 10/2005 |
| WO | 2007062118 A2 | 5/2007 |
| WO | 2007094922 A2 | 8/2007 |
| WO | 2009032905 A1 | 3/2009 |

OTHER PUBLICATIONS

Chirila, Traian, "Cicloacetal-esteri penta-se hexaatomici", Revista de Chimie 28(8), 730-733 (1977) [with English abstract].
Chopade et al., "Acetalization of ethylene glycol with formaldehyde using cation-exchange resins as catalysts: batch versus reactive distillation", Reactive & Functional Polymers 34 (1997) pp. 37-45.
Clarkson et al., "Continuous Reactor Technology for Ketal Formation: An Improved Synthesis of Solketal", Organic Process Research & Development, 5, 2001, pp. 630-635.
Clerici et al., "Efficient Acetalisation of Aldehydes Catalyzed by Titanium Tetrachloride in a Basic Medium", Tetrahedron 54, (1998), pp. 15679-15690.
Deutsch, et al., Investigations on heterogeneously catalysed condensations of glycerol to cyclic acetals, Journal of Catalysis 245: 428-435 (2007).
Gasparrini, F., "Synthesis of Dimethyl Acetals, Diethyl Acetals, and Cyclic Acetals Catalyzed by Aminopropylated Silica Gel Hydrocholoride(APSG-HCL)", Tetrahedron 40(9), (1984) p. 1491-1500.
Gelas, Jacques and Thiallier, Andre, "Synthese du 4-oxo et de 4-hydroxy-3,6,8-trioxabicyclo[3.2.1]octanes", Carbohydrate Research 30(1), 1973, p. 21-34 1973 (with English abstract).
Grabarnick et al., On five-species; Mar. 2000; American Chemical Society; Chem Abstract 132: 308566, 2 pages.
Grajkowski, Andrzej et al., "Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group", J. Org. Chem, 2007, vol. 72, No. 3, 805-815.
Hachihama, Yoshikazu; Hayashi, Izumi, "Studies on the Preparation of Plasticizers from Carbohydrate Sources ", Technology Reports of the Osaka University (1953), 3, 191-200.
Hiltunen, et al., Synthesis and Characterization of Lactic Acid Based Telechelic Prepolymers, Macromolecules 29: 8677-8682 (1996).
Hoydonckx, et al., "Esterification and transesterification of renewable chemicals," Topics in Catalysis 27(1-4): 83-96 (2004).
Imwinkelried et al., "Diisopropyl (2S,3S)-2,3-O,Isoprophylidenetartrate", Organic Syntheses, Coll. vol. 8, p. 201 (1993); vol. 65, p. 230 (1987).
International Preliminary Report on Patentability for PCT/US2011/060452 dated May 23, 2013, 7 pages.
Kim, et al., "Preparation of High-Molecular-Weight Poly(L-lactic acid)-Based Polymers Through Direct Condensation Polymerization in Bulk State," Journal of Applied Polymer Science 100: 466-472 (2006).
Lenz et al.; poly(ester-acetals)-azelaaldehydate; May 1984; American Checmial Society; Chem Abstract 70:97280, 3 pages.
Lenz et al.; Structure—poly(acetals); May 1984; Macromolecules (1969), 2(2), 129-36.
Lenz et al.; Structure—repeating units; May 1984; American Chemical Society; Chem Abstract 72; 122322, 4 pages.
Li, Tong-Shuang, et al., "Montmorillonite Clay Catalysis. Part 2. An Efficient and Convenient Procedure for the Preparation of Acetals Catalysed by Montmorillonite K-10," J. Chem Research (S) 26-27 (1997).
Meher, et al., "Technical aspects of biodiesel production by transesterification—a review," RSER 194: 1-21 (2004).
Meskens, Frans A. J., Methods for the Preparation of Acetals from Alcohols or Oxiranes and Carbonyl Compounds, Synthesisn (1981) 501-522.
Nagahata, et al., "Solid-Phase Thermal Polymerization of Macrocyclic Ethylene Terephthalate Dimer Using Various Transesterification Catalysts," Journal of Polyer Science: Part A: Polymer Chemistry 38: 3360-3368 (2000).
Nagata et al., "Synthesis and Applications of [2-Methyl-2(oxoalkyl)-1,3-dioxolan-4-yl] methyl Acrylates for Photocrosslinking Agent", Osaka Kogyo Gijutsu Shikensho Kiho 37(1): 8-16 (1986); with English Abstract.
Nakamura et al. "Study on Ketalization Reaction of Poly(vinyl alcohol) by Ketones.IX.Kinetic Study on Acetalization and Ketalization Reaction of 1,3-Butanediol as a Model Compound for Poly(vinyl alcohol)",J.Polym.Sci A: Polym Chem35, pp. 1719-1731, 1997.
Newman et al., "Kinetic and Equilibrium Studies of Cyclic Ketal Formation and Hydrolysis", J. Am. Chem. Soc., 1958, 80 (23), pp. 6350-6355.
Ono et al., "Preparation, Surface-Active Properties and Acid Decomposition Profiles of a New 'Soap' Bearing a 1,3-Dioxolane Ring", JAOCS, vol. 70, No. 1, 1993, pp. 29-36.
Otera, "Esterificaton: Methods, Reactions, and Applications", Wiley-VCH Verlag GmbH & Co., (2003) 19 pages.
Pang, et al., "Review of conventional and novel polymerization processes for polyesters," Prog. Polym. Sci. 31: 1009-1037 (2006).
Pasto et al., "Neighboring Group Participation by Carbonyl Oxygen", J. Amer. Chem. Soc., 87(7) (1965) pp. 1515-1521.
Patel et al., "Ketalization of ketones with diols catalyzed by metal (IV) phosphates as solid acid catalysts," Journal of Molecular Catalysis A: Chemical 194: (2003) pp. 267-271.
Piantadosi et al., "The Preparation of Cyclic Glycerol Acetals by Transacetalation," J. Am. Chem. Soc., 1958, 80(24), pp. 6613-6617.
Showler et al., "Condensation Products of Glycerol with Aldehydes and Ketones. 2-Substituted m-Dioxan-5-OLS and 1,3-dioxolane-4-methanols," Chem. Rev. 1967, 67 (4), pp. 427-440.
Smith et al., "The gem-Dialkyl Effect. III. Kinetic and Equilibrium Studies of Steroid Cyclic Ketal Formation and Hydrolysis", Journal of the American Chemical Society (1968) 90(5): pp. 1253-1257.
Smith, M., Mechanisms, and Structure, 2007, Wiley Interscience, Chapter 16, p. 1251-1274.
Sodergard, et al., "Properties of lactic acid based polymers and their correlation with composition," Prog. Polym. Sci. 27: 1123-1163 (2002).
Transmittal and International Search Report for PCT/US2011/060452, dated Jul. 2, 2012, 6 pages.
Vermylen, et al., "Study of the Thermal Evolution of the Cyclic-Oligomer Formation in a Cyclic-Oligomer-Free PET," Journal of Polymer Science: Part A: Polymer Chemistry 38: 416-422 (2000).
Wang et al., "An efficient procedure for protection of carbonyls catalyzed by sulfamic acid", Journal of Molecular Catalysis A: Chemical 233 (2005), pp. 121-126.
Wood et al., "Cyclic polyesters: 1. Preparation by a new synthetic method, using polymer-supported reagents", Polymer 34 (14): (1993) pp. 3052-3058.
Written Opinion of the International Searching Authority for PCT/US2011/060452, dated Jul. 2, 2012, 5 pages.
Wuts, Peter G.M., Greene's Protective Groups in Organic Synthesis, 2006, Fourth Edition, John Wiley and Sons, Chapter 5, p. 533-646.

(56) References Cited

OTHER PUBLICATIONS

Xu et al., "The use of polymer supports in organic synthesis. XXVIII. The monoblocking of symmetrical diketones on insoluble polymer supports", Canadian Journal of Chemistry, vol. 61, No. 7, (1983), pp. 1405-1409.

Yamada, Tatsuhiko et al., "Characterization of the products resulting from ethylene glycol liquefaction of cellulose", J. Wood Sci. 2001, vol. 47, 458-464.

POLYHYDROXY KETAL ESTER ADDUCTS, METHODS OF MANUFACTURE AND USES THEREOF

CROSS-REFERENCE TO RELATED APPLICATION

This application is a divisional of U.S. patent application Ser. No. 13/294,854, filed on Nov. 11, 2011, which claims the benefit under 35 U.S.C. 119(e) of U.S. Provisional Application Ser. No. 61/412,699, filed on Nov. 11, 2010, the contents of both of which are incorporated by reference herein in their entirety.

BACKGROUND

This disclosure relates to polyhydroxy ketal adducts, their method of manufacture, and uses thereof.

Many known chemical products such as surfactants, plasticizers, solvents, and polymers are currently manufactured from non-renewable, expensive, petroleum-derived, or natural gas-derived feedstock compounds. High raw material costs and uncertainty of future supplies requires the discovery and development of surfactants, plasticizers, solvents, and polymers that can be made from inexpensive renewable biomass-derived feedstocks and by simple chemical methods.

SUMMARY

The inventors hereof have discovered methods for the manufacture of chemical additives, in particular ketal polyol adducts, for use in polymeric formulations as well as in the production of polymers. The methods make use of biosourced feedstocks, in particular polyols and oxocarboxylic acids such as pyruvic, acetoacetic, and levulinic acid and their related derivatives. These compounds can be sourced from renewable, non-petroleum feedstocks that can be prepared on an industrial scale. Chemical products produced from these two types of materials can fill a need for inexpensive, renewable consumer and industrial products not based on petroleum or other nonrenewable resource.

Accordingly, disclosed herein is a method for the manufacture of a polyketal adduct I

I wherein
G is a polyester, polyether, polycarbonate, or a C2-32 hydrocarbylene group having a valence t, wherein t=2-12,
each $R^2$ is independently C1-6 alkyl,
each $R^3$, $R^4$, and $R^6$ are each independently hydrogen, C1-6 alkyl, —$OR^8$ wherein $R^8$ is C1-4 alkyl, or —$C(O)R^9$ wherein $R^9$ is C1-4 alkyl,
each $R^7$ is independently C1-6 alkylene, or C1-6 alkylene substituted with one —$OR^8$ group wherein $R^8$ is C1-3 alkyl, or —$C(O)R^9$ wherein $R^9$ is C1-2 alkyl, each a is independently=0-3,
each b is independently=0-1,
each m is independently=1-50,
p=0-11,
q−n=0-11, and
n=1-12, provided that p+n≥2, q≥n, and p+(q−n)+n=t, wherein t=2-12, and is the valence of G,
the method including
(a) esterifying a polyol II $$G\text{-}[OH]_t \quad\quad II$$

with a ketocarboxy compound III

III wherein L is hydroxy, halide, —OC(=O)$R^{11}$, or —$OR^{11}$ wherein $R^{11}$ is a C1-4 alkyl, in the presence of an esterification catalyst, to form a ketocarboxylic ester IV

IV wherein p=0-11 and q=1-12, provided p+q≥2, and p+q=t; and (b) ketalizing ketocarboxylic ester IV with an excess of polyol V

V in the presence of a ketalization catalyst to provide the ketal adduct I.

Further disclosed is a composition including essentially no transition metal; and a polyhydroxy ketal adduct I

I wherein
G is a polyester, polyether, polycarbonate, or a C2-32 hydrocarbylene group, each having a valence of t, wherein t=2-12,
each $R^2$ is independently C1-6 alkyl,
each $R^3$, $R^4$, and $R^6$ is each independently hydrogen, C1-6 alkyl, —$OR^8$ wherein $R^8$ is C1-4 alkyl, or —$C(O)R^9$ wherein $R^9$ is C1-4 alkyl, each $R^7$ is independently C1-6 alkylene or C1-6 alkylene substituted with one —$OR^8$ group wherein $R^8$ is C1-3 alkyl, or —$C(O)R^9$ wherein $R^9$ is C1-2 alkyl, each a is independently=0-3,
each b is independently=0-1,
each m is independently=1-50,
q−n=0-10, and
n=1-12, provided that p+n≥2, q≥n, and p+(q−n)+n=t.

In another aspect, a polymer composition includes a polymer; and the polyhydroxyketal ester adduct I or composition as described above.

In still another aspect, a polyester includes ester units derived from polymerization of a carboxylic diacid and the polyhydroxyketal ester adduct I or composition as described above.

In another aspect, a polycarbonate includes carbonate units derived from polymerization of a carbonate precursor and the polyhydroxy ketal adduct I or composition as described above.

In another aspect, a polyurethane includes urethane units derived from polymerization of a polyisocyanate and the polyhydroxy ketal adduct I or composition as described above.

Articles including the polymer formulations are also disclosed.

In an aspect, a coating composition comprises a polymer binder; an aqueous phase; and the polyhydroxy ketal adduct I. A method of preparing the coating composition comprises combining the polymer binder, the polyhydroxy ketal adduct I or composition of claims 1-29, and the aqueous phase.

In another aspect, a coated substrate comprises a substrate having a surface; and a coating disposed on the surface, wherein the coating comprises a polymer binder; optionally a pigment or a dye; and polyhydroxy ketal ester adduct I. The coatings can be paints, inks, stains, caulks, and clearcoats, for example. A method of coating a substrate comprises contacting a coating composition comprising polyhydroxy ketal ester adduct I with a surface of the substrate to form a coating; and drying the coating.

DETAILED DESCRIPTION

The inventors hereof have found that polyhydroxy ketal ester adducts I can be efficiently produced by a process wherein a polyol II is esterified with a ketocarboxylic acid (or derivative thereof) to produce a ketocarboxylic ester, which is then ketalized to produce the polyhydroxy ketal ester adduct I. In a particularly advantageous aspect, both the hydrocarbon polyol and the ketocarboxy can be biosourced. In another aspect, the polyhydroxy ketal ester adducts I can be synthesized economically in large volumes. A still further advantage is that the adducts can be manufactured in high purity.

In a specific embodiment of this process, a diol, is monoesterified with a ketocarboxylic acid to produce a monoketocarboxylic ester, and in another embodiment, a triol is diesterified with a ketocarboxylic to produce a diketocarboxylic ester. Higher polyols with different degrees of esterification can be used. The ketone groups are then ketalized to produce the polyhydroxy ketal ester adduct I. In an embodiment, each ketone group is ketalized. Advantageously, the polyol, e.g., the diol or the triol, and/or the ketocarboxylic acid can be biosourced. In another advantageous aspect, the process can proceed continuously without isolation of the intermediate ketocarboxylic ester. In still another advantageous feature, the polyhydroxyketal ester adduct I can be obtained in high purity, for example with lower amounts of oligomeric species.

The method for the manufacture of the polyhydroxy ketal adduct I comprises esterifying a polyol II $$G\text{-}[OH]_t \qquad \text{II}$$

wherein G is a hydrocarbylene group having at least two carbons and a valence of t, wherein t=2-12. In an embodiment, G is a polymeric polyol, in some embodiments a diol, comprising 2 or more ester, carbonate, or ether repeat units, for example 2-1,000, 5-500, or 10-100 repeat units. Polyols known in the art include those described in *Szycher's Handbook of Polyurethanes*, Michael Szycher (CRC Press LLC 1999) which is incorporated by reference herein in its entirety. Exemplary polyester polyols include those used in the manufacture of polyesters and polyurethanes for example, and include aliphatic polyester polyols, polycaprolactone polyols and aromatic polyester polyols, diethyleneglycol phthalate polyols, such as those produced by the INVISTA™ Company of Wichita, Kans. under the trade name Terate®. Exemplary polycarbonate polyols include those used in the manufacture of polycarbonates, for example, and include those having bisphenyl units, in particular bisphenol A units. Other polycarbonate polyols include those derived from aliphatic polycarbonates including ethylene, propylene, butylene, and hexylene carbonate units. Exemplary polyether polyols include those used in the manufacture of polyesters or polyurethanes, where the ethers can contain, for example, C1-6 straight chain or branched alkylene groups, including mixtures thereof. The foregoing polyols are commercially available and can be prepared by known techniques. Commercially available polyols include polyester diols derived from adipic acid and butane diol, succinic acid and diethylene glycol of varying molecular weights, such as Desmophen available from the Bayer® Corporation (Pittsburg, Pa.). Other polyester diols may be used, such as those derived from 1,3 propane diol, such as CERENOL available from DuPont® Corporation (Wilmington, Del.). Commercially available polyols also include polycarbonate diols of varying molecular weights, such as L467m, L600m, and L565m, available from Asahi Kasei Corporation (Tokyo, Japan); the polyether polyols based on ethylene glycol, for example CARBOWAX® polyethylene glycols (available from The Dow® Chemical Company of Midland, Mich.), polyether diols and polyols based on propylene glycol or combinations of ethylene glycol and propylene glycol, such as those sold by the Dow® Chemical Company of Midland, Mich. under the trade name VORANOL, for instance, and polyether glycols such as those produced by the INVISTA™ Company of Wichita, Kans. under the trade name TERETHANE®; and polyols based on hydroxylated vegetable oils, such as those sold under the trade name BiOH®, available from the Cargill Company of Wayzata, Minn.; and the polyols employed in the Union Carbide Company (South Charleston, W. Va.) publication by Carey, Mass. et al., "Rapid Method for Measuring the Hydroxyl Content of Polyurethane Polyols" (published on the internet at http://www.polyurethane.org/s_api/doc_paper.asp?CE)="1044&DID=4060, accessed on Nov. 9, 2010).

G can also be a C2-32 alkylene, C2-32 alkenylene, C4-8 cycloalkylene, C5-8 cycloalkenylene, C6-12 arylene, or C2-32-$(R^{12}O)_u R^{12}$— wherein each $R^{12}$ is methylene, ethylene, 1,3-propylene, or 1,2-propylene and u=1-31; specifically C2-8 alkylene, C2-8 alkenylene, C6-12 arylene, or C4-16-$(R^{12}O)_u R^{12}$— wherein each $R^{12}$ is independently ethylene, 1,3-propylene, or 1,2-propylene, and u=1-7; or more specifically C2-8 alkylene or C4-9-$(R^{12}O)_u R^{12}$— wherein each $R^{12}$ is independently ethylene, 1,3-propylene, or 1,2-propylene, and u=1-2; or more specifically C2-6 alkylene or —(CH$_2$CH$_2$OCH$_2$CH$_2$)—; or more specifically C2-16 alkylene, C2-16 alkenylene, C6-12 arylene, or C2-16-(R$^{12}$O)$_u$R$^{12}$— wherein R$^{12}$ is ethylene or 1,3-propylene, and u=1-15; or more specifically C2-6 alkylene or C4-12-(R$^{12}$O)$_u$R$^{12}$— wherein R$^{12}$ is ethylene or 1,3-propylene and q=1-5; or more specifically C2-6 alkylene or C4-10-(R$^{12}$O)$_u$R$^{12}$— wherein R$^{12}$ is ethylene and u=1-4.

Hydrocarbon polyol II is esterified with a ketocarboxy compound III

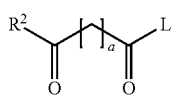

wherein a combination of different ketocarboxy compounds III can be used. In formula III, L can be hydroxy, halide, —OC(=O)R$^{11}$, or —OR$^{11}$ wherein R$^{11}$ is a C1-4 alkyl. Further R$^2$ is C1-6 alkyl, specifically C1-4 alkyl, C1-3 alkyl, more specifically a C1-2 alkyl, even more specifically methyl. Further in formula III, a=0-3, more specifically 1-2, still more specifically 2. When a is 0, a single bond connects the two carbonyl groups. Also in formula III, L is a hydroxy, halide, or —OR$^{11}$ wherein R$^{11}$ is a $C_1$-$C_3$ alkyl. In a specific embodiment L is hydroxy.

Esterification occurs in the presence of no added catalyst (the ketocarboxy compound III can function as a catalyst), an acid esterification catalyst, or a base if L is a halide as described in further detail below. Esterification produces a polyketocarboxylic ester IV

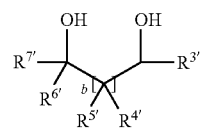

wherein R$^2$ and a are as in the ketocarboxy compound III, p+q=t wherein t is the valence of G in hydrocarbon polyol II, and q≥p. In some embodiments, q=t, i.e., all hydroxyl groups in polyol I have been esterified. In other embodiments, the value of q is less than the value of t, i.e., one, two, three, or more hydroxyl groups remain unreacted. The reactivity of polyol II, the equivalents of ketocarboxy compound III used in the esterification, and the esterification conditions can be selected to achieve the desired value of q, i.e., q=1-12 (depending on the value of t), specifically 1-10, or 1-8, or 1-6, 1-5, or 1-4, or 1-3, or 2, or 1. As described below, this product can be used as synthesized or further purified.

Esterification is followed by ketalizing the ketocarboxylic ester IV with a molar excess of a polyol V

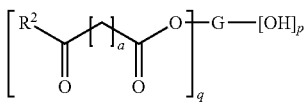

wherein a combination of two or more different polyols V can be used. In an embodiment, the same (i.e., one) type of polyol V is used. In formula V, each R$^3$, R$^4$, and R$^6$ can independently be hydrogen, C1-6 alkyl, —OR$^8$ wherein R$^8$ is C1-4 alkyl, or —C(O)R$^9$ wherein R$^9$ is C1-4 alkyl; or each R$^3$, R$^4$, and R$^6$ is independently hydrogen or C1-3 alkyl. Each R$^7$ is independently C1-6 alkylene or C1-6 alkylene substituted with one —OR$^8$ group wherein R$^8$ is C1-3 alkyl, or —C(O)R$^9$ wherein R$^9$ is C1-2 alkyl; or each R$^7$ is independently C1-6 alkylene. Also, b in formula V can be 0-1, specifically 0. When b is 0, the carbon bearing R$^6$ is directly linked to the carbon bearing R$^3$. Specific polyols V include glycerol and trimethylolpropane (TMP).

It is also possible to use diols in combination with the foregoing polyols. Use of a combination of a polyol V and a diol VI allows adjustment of the number of hydroxyl end groups in ketal I, i.e., the number of hydroxy endgroups can be decreased by using a higher proportion of polyol V to diol. Such diols can be of the formula VI

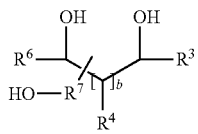

wherein a combination of different diols VI can be used. In an embodiment, the same diol VI is used.

In formula VI, b is 0 or 1. When b is 0, the carbon bearing R$^3$ is directly linked to the carbon bearing R$^{6'}$ and R$^{7'}$. R$^{3'}$ in formula VI is hydrogen or $C_1$-$C_6$ alkyl, specifically hydrogen or $C_1$-$C_3$ alkyl, more specifically hydrogen. R$^{4'}$ and R$^{5'}$ in formula VI are each independently hydrogen or $C_1$-$C_6$ alkyl, specifically hydrogen or $C_1$-$C_3$ alkyl. R$^{6'}$ in formula VI is hydrogen or $C_1$-$C_6$ alkyl, specifically hydrogen or $C_1$-$C_3$ alkyl. Further, R$^{3'}$ and R$^{6'}$ together with their directly attached carbons can form a fused cycloaliphatic or aromatic ring having a total of 5-6 carbon atoms or 4-5 carbon atoms and 1-2 oxygen atoms, specifically a fused cycloaliphatic or aromatic ring having a total of 5-6 carbon atoms. R$^{7'}$ in formula VI is hydrogen, $C_1$-$C_6$ alkyl, or R$^{7'}$ is $C_5$-$C_6$ cycloalkyl that is optionally substituted with an oxygen in the ring and further optionally substituted with or OR$^{10}$ wherein R$^{10}$ is $C_1$-$C_3$ alkyl. In a specific embodiment, R$^{7'}$ is hydrogen or $C_1$-$C_4$ alkyl, more specifically hydrogen or $C_1$-$C_3$ alkyl, still more specifically methyl.

Ketalization with polyol (V), optionally in the presence of a ketalization catalyst, provides the polyhydroxy ketal adduct I

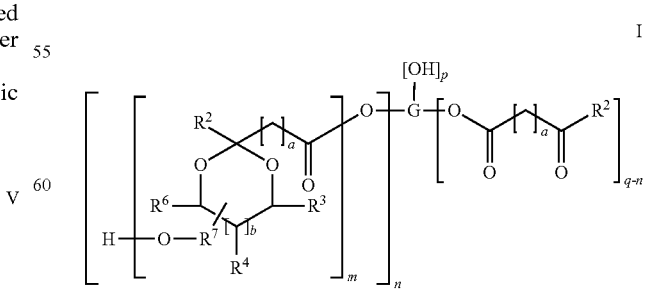

wherein each of G, R$^2$, R$^3$, R$^4$, R$^6$, and R$^7$, a and b are as defined in formulas II, III, IV, and V. In formula I, p+n+(q− n)=p+q=t, wherein t is the valence of G, i.e., 2-12. In an embodiment, p=0-11, q−n=0 to 10, and n=1-12, specifically p=0-10, q−n=0 to 9, and n=1-11, more specifically p=0-9, q−n=0 to 8, and n=1-10, or p=0-7, q−n=0 to 6, and n=1-8, provided that p+n≥2, and q≥n.

In a specific embodiment, the ketone groups of the ketocarboxy ester group are fully ketalized, that is, q=n.

In another specific embodiment, all of the hydroxyl groups of polyol II are esterified, that is, p=0.

In still another specific embodiment, all of the ketone groups of the ketocarboxy ester group are fully ketalized, and all of the hydroxy groups of polyol II are esterified, that is, p=0 and q=n.

In a specific embodiment with reference to each of formulas II, III, IV, V, and polyhydroxy ketal adduct I, G is a linear or branched polyether, polyester, or polycarbonate polyol having from 1-1,000 repeat units or a C2-32 hydrocarbylene group, each $R^2$ is independently C1-6 alkyl, each $R^3$, $R^4$, and $R^6$ are each independently hydrogen, C1-6 alkyl, —$OR^8$ wherein $R^8$ is C1-4 alkyl, or —$C(O)R^9$ wherein $R^9$ is C1-4 alkyl, each $R^7$ is independently C1-6 alkylene, or C1-6 alkylene substituted with one —$OR^8$ group wherein $R^8$ is C1-3 alkyl, or —$C(O)R^9$ wherein $R^9$ is C1-2 alkyl, each a is independently=0-3, each b is independently=0-1, each m is independently=1-50, p=0-11, and q−n=0-10, and n=1-12, provided that p+n≥2, q≥n, and p+(q−n)+n=t, wherein t is the valence of G, and wherein t=2-12. In this embodiment, each ketocarboxy compound III and polyol V can be the same or different. Preferably, each ketocarboxy compound III and polyol V is the same.

In another specific embodiment with reference to each of formulas II, III, IV, V, and polyhydroxy ketal adduct I, G is C2-32 alkylene, C2-32 alkenylene, C4-8 cycloalkylene, C5-8 cycloalkenylene, C6-12 arylene, or C2-32-($R^{12}$O)—$R^{12}$— wherein each $R^{12}$ is methylene, ethylene, 1,3-propylene, or 1,2-propylene and u=1-31, each $R^2$ is independently C1-3 alkyl, each $R^3$, $R^4$, and $R^6$ is each independently hydrogen or C1-3 alkyl, each $R^7$ is independently C1-6 alkylene, each a is independently=0-3, each b is independently=0-1, each m is independently=1-40, p=0-11, and q−n=1-10, and n=1-12, provided that p+n≥2, q≥n, and p+(q−n)+n=t, wherein t is the valence of G, and wherein t=2-12. In this embodiment, each ketocarboxy compound III and polyol V can be the same or different. Preferably, each ketocarboxy compound III and polyol V is the same.

In another specific embodiment with reference to each of formulas II, III, IV, V, and polyhydroxy ketal adduct I, G is C2-8 alkylene, C2-8 alkenylene, C6-12 arylene, or C4-16-($R^{12}$O)$_u$$R^{12}$— wherein each $R^{12}$ is independently ethylene, 1,3-propylene, or 1,2-propylene, and u=1-7, each $R^2$ is independently C1-3 alkyl, each $R^3$, $R^4$, and $R^6$ is independently hydrogen or C1-3 alkyl, each $R^7$ is independently C1-6 alkylene, each a is independently=0-3, each b is independently=0-1, each m is independently 1-30, p=0-11, and q−n=0-10, and n=1-12, provided that p+n≥2, q≥n, and p+(q−n)+n=t, wherein t is the valence of G, and wherein t=2-12. In this embodiment, each ketocarboxy compound III and polyol V can be the same or different. Preferably, each ketocarboxy compound III and polyol V is the same.

In yet another specific embodiment, with reference to each of formulas II, III, IV, V, and polyhydroxy ketal adduct I, p=0-9, and q−n=1-8, and n=1-10, provided that p+n≥2, q≥n, and p+(q−n)+n=t, wherein t is the valence of G, and wherein t=2-12 or 2-6. In this embodiment, each ketocarboxy compound III and polyol V can be the same or different. Preferably, each ketocarboxy compound III and polyol V is the same.

In yet another specific embodiment, with reference to each of formulas II, III, IV, V, and polyhydroxy ketal adduct I, p=0-7, and q−n=1-6, and n=1-8, provided that p+n≥2, q≥n, and p+(q−n)+n=t, wherein t is the valence of G, and wherein t=2-12 or 2-6. In this embodiment, each ketocarboxy compound III and polyol V can be the same or different. Preferably, each ketocarboxy compound III and polyol V is the same.

In a specific embodiment, the polyhydroxy ketal ester adduct I is fully ketalized such that q−n=0, and the adduct has the formula Ia

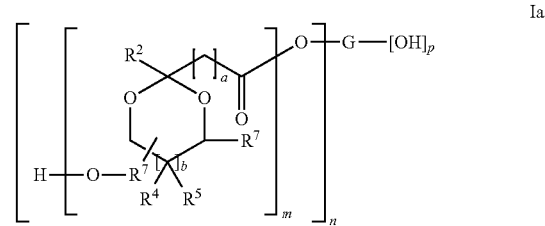

wherein G is C2-8 alkylene or C4-9-($R^{12}$O)$_u$$R^{12}$— wherein each $R^{12}$ is independently ethylene, 1,3-propylene, or 1,2-propylene, and u=1-2, $R^2$ is C1-3 alkyl, each $R^3$, $R^4$, and $R^6$ is each independently hydrogen or C1-3 alkyl, each $R^7$ is independently C1-6 alkylene, each a is independently=1-2, each b is independently=0-1, each m is independently=1-20, p=0-11, and n=1-12, provided that p+n≥2, and p+n=t, wherein t is the valence of G, and wherein t=2-12 or 2-6.

In another specific embodiment with reference to each of formulas II, III, IV, V, and polyhydroxy ketal adduct Ia, G is a C2-6 alkylene or —($CH_2CH_2OCH_2CH_2$)—, $R^2$ is methyl, each $R^3$, $R^4$, and $R^6$ is each independently hydrogen or C1-3 alkyl, each $R^7$ is independently C1-6 alkylene, m=1 to 5, and either n=1 and p=1, or n=2 and p=0. In this embodiment, each ketocarboxy compound III and polyol V can be the same or different. Preferably, each ketocarboxy compound III and polyol V is the same.

When levulinic acid IIIa is used,

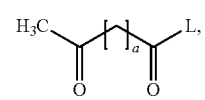

the ketocarboxylic ester IVa

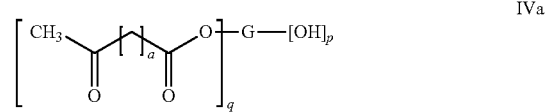

is formed, and $R^2$ in polyhydroxy ketal ester adduct I is methyl as shown in formula Ib

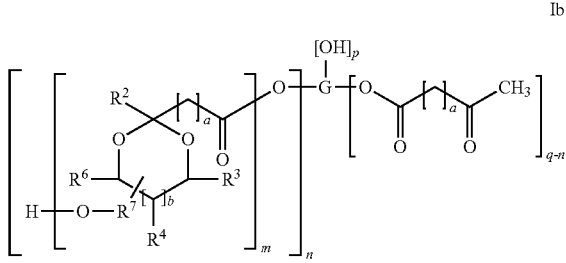

wherein G, each $R^3$, $R^4$, $R^6$, $R^7$, a, b, p, and q are a described in polyhydroxyketal I above, including the specific embodiments. For example, G is a C2-6 alkylene or —(CH$_2$CH$_2$OCH$_2$CH$_2$)—, each $R^3$, $R^4$, and $R^6$ is each independently hydrogen or C1-3 alkyl, each $R^7$ is independently C1-6 alkylene, m=1 to 5, and either n=1 and p=1, or n=2 and p=0.

In another specific embodiment, the polyhydroxy ketal ester adduct I has the formula Ic

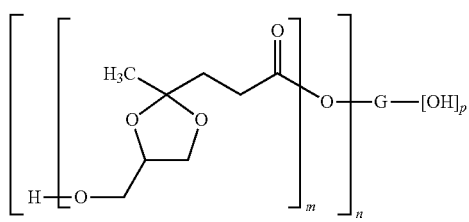

wherein G is C2-32 alkylene, C2-32 alkenylene, C4-8 cycloalkylene, C5-8 cycloalkenylene, C6-12 arylene, or C1-32-$(R^{12}O)_uR^{12}$— wherein each $R^{12}$ is independently methylene, ethylene, 1,3-propylene, or 1,2-propylene, and u=1-31, each m independently=1-50, n=1-5, and p=0-5, provided that p+n=t, wherein t is the valence of G, and wherein t=2-12 or 2-6.

In another specific embodiment with reference to each of formulas II, III, IV, V, and polyhydroxy ketal adduct Ic, G is C2-16 alkylene, C2-16 alkenylene, C6-12 arylene, or C2-16-$(R^{12}O)_uR^{12}$— wherein $R^{12}$ is ethylene or 1,3-propylene, and u=1-15, each m is independently=1-40, p=0-4, and n=1-5, provided that p+n=2-5. In this embodiment, each ketocarboxy compound III and polyol V can be the same or different. Preferably, each ketocarboxy compound III and polyol V is the same.

In another specific embodiment with reference to each of formulas II, III, IV, V, and polyhydroxy ketal adduct Ic, G is C2-6 alkylene or C4-12-$(R^{12}O)_qR^{12}$— wherein $R^{12}$ is ethylene or 1,3-propylene and q=1-5, each m is independently=1-30, p=0-3, and n=1-4, provided that n+p=2-4. In this embodiment, each ketocarboxy compound III and polyol V can be the same or different. Preferably, each ketocarboxy compound III and polyol V is the same.

In another specific embodiment with reference to each of formulas II, III, IV, V, and polyhydroxy ketal adduct Ib, G is C2-6 alkylene or C4-10-$(R^{12}O)_uR^{12}$— wherein $R^{12}$ is ethylene and u=1-4, m=1-20, p=0-2, and n=1-3, provided that n+p=2-3. In this embodiment, each ketocarboxy compound III and polyol V can be the same or different. Preferably, each ketocarboxy compound III and polyol V is the same.

In another specific embodiment with reference to each of formulas II, III, IV, V, and polyhydroxy ketal adduct Ic, G is C2-6 alkylene or C4-10-$(R^{12}O)_uR^{12}$— wherein $R^{12}$ is ethylene and u=1-4, each m is independently=1-10, p=0, and n=1-3. In this embodiment, each ketocarboxy compound III and polyol V can be the same or different. Preferably, each ketocarboxy compound III and polyol V is the same.

In another specific embodiment with reference to each of formulas II, III, IV, V, and polyhydroxy ketal adduct Ic, G is a C2-6 alkylene or —(CH$_2$CH$_2$OCH$_2$CH$_2$)—, each m is independently=1 to 10, and n=1 and p=1, or n=2 and p=0. In this embodiment, each ketocarboxy compound III and polyol V can be the same or different. Preferably, each ketocarboxy compound III and polyol V is the same.

In another specific embodiment, the polyol is an alkylene diol of the formula IIa HO-G-OH  IIa wherein G is a C2-6 alkylene, specifically a C2-4 alkylene. 1,4-Butanediol ("BDO"), 1,6-hexanediol ("HDO"), 1,3-propane diol (PDO) and diethylene glycol ("DEG") can be specifically mentioned. The diol IIa is esterified by reaction with a ketocarboxylic acid IIIa (levulinic acid)

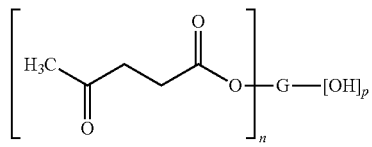

in the presence of a catalyst, to produce a mono or diketocarboxylic ester IVa

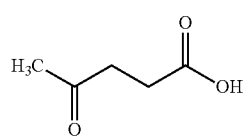

wherein G is a C2-6 alkylene, or C4-6 alkenylene, specifically a C2-4 alkylene, and either n=1 and p=1, or n=2 and p=0. An embodiment wherein G is 1,4-butylene, 1,6-hexylene, or —CH$_2$CH$_2$OCH$_2$CH$_2$— is specifically mentioned. Ketalizing the ketocarboxylic ester IV with glycerol, in the presence of a ketalization catalyst, provides the polyhydroxy ketal ester adduct Id

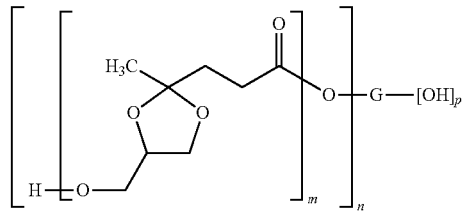

wherein G is a C2-6 alkylene, specifically a C2-4 alkylene, each m=1-50, specifically 1-20, or 1-10, or 1-5, and either n=1 and p=1, or n=2 and p=0. An embodiment wherein G is 1,4-butylene, 1,6-hexylene, or —CH$_2$CH$_2$OCH$_2$CH$_2$— is specifically mentioned. Specific compounds within the scope of Id include the monoester adducts Ie and If and the diester adducts Ig and Ih:

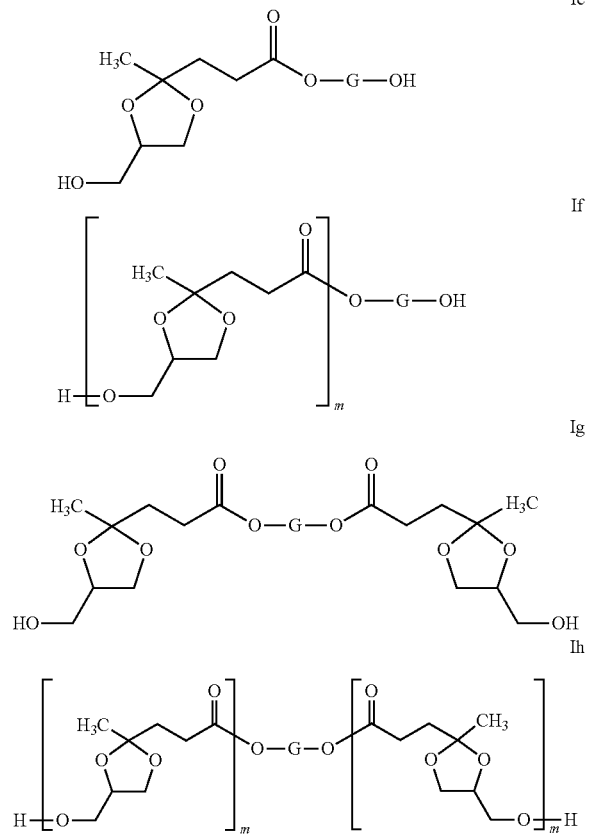

wherein G is a C2-6 alkylene, specifically a C2-4 alkylene or hexylene, more specifically butylene, ethylene, or —(C2H5)-O—(C2H5)-, and each m=1-50, specifically 1-20, more specifically 1-10, or 1-5.

In an embodiment, in one method of manufacturing the polyhydroxy ketal adduct I, the hydrocarbon polyol II along with the ketocarboxy compound III and an acid catalyst are charged to a reactor. The ratio of polyol and equivalents of ketocarboxy compound III will depend on the desired degree of esterification of the polyol. In an embodiment, particularly where complete esterification is desired, the molar ratio of the ketocarboxy acid III to the hydrocarbon polyol II is greater than or equal to about 1.5:1, specifically greater than or equal to about 1.7:1 and more specifically greater than or equal to about 2.0:1.

The amount of polyol V depends on the desired degree of ketalization, and is generally present in a stoichiometric excess over the ketocarboxylic ester IV. In an embodiment, the molar ratio of the polyol V to the ketocarboxylic ester IV is greater than or equal to about 2, specifically greater than or equal to about 2.5 and more specifically greater than or equal to about 3.

The esterification and/or ketalization can be conducted in the presence of an optional acid catalyst, which can be either a Lewis or Brønsted-Lowry acid. Acid catalysts that are known homogeneous catalysts for either ketal formation or esterification or transesterification reactions can be used, for example strong protic acid catalysts, e.g., Brønsted-Lowry acids that have a Ka of 55 or greater. Examples of strong protic acid catalysts include sulfuric acid, arylsulfonic acids, and hydrates thereof such as p-toluenesulfonic acid monohydrate, methane sulfonic acid, camphor sulfonic acid, dodecyl benzene sulfonic acid, perchloric acid, hydrobromic acid, hydrochloric acid, 2-naphthalene sulfonic acid, and 3-naphthalene sulfonic acid. In other embodiments, weak protic acid catalysts, e.g., having a Ka of less than 55, can be used, for example phosphoric acid, orthophosphoric acid, polyphosphoric acid, and sulfamic acid. Aprotic (Lewis acid) catalysts can include, for example, titanium tetraalkoxides, aluminum trialkoxides, tin (II) alkoxides, carboxylates, organo-tin alkoxides, organo-tin carboxylates, and boron trifluoride. A combination comprising any one or more of the foregoing acid catalysts can be used. In some embodiments, the method employs a substantially nonvolatile acid catalyst such that the acid does not transfer into the distillate, such as sulfuric or sulfamic acid. In an exemplary embodiment, the homogenous catalyst is camphor sulfonic acid.

Instead of, or in addition to the homogenous acid catalyst, a heterogenous acid catalyst can be used, where the acid catalyst is incorporated into, onto, or covalently bound to, a solid support material such as resin beads, membranes, porous carbon particles, zeolite materials, and other solid supports. Many commercially available resin-based acid catalysts are sold as ion exchange resins. One type of useful ion exchange resin is a sulfonated polystyrene/divinyl benzene resin, which supplies active sulfonic acid groups. Other commercial ion exchange resins include LEWATIT® ion exchange resins sold by the Lanxess Company of Pittsburgh, Pa.; DOWEX™ ion exchange resins sold by the Dow Company of Midland, Mich.; and AMBERLITE® and AMBERLYST® ion exchange resins sold by the Dow Company of Midland, Mich. In embodiments, AMBERLYST® 15, AMBERLYST® 35, AMBERLYST® 70 are used. In embodiments, NAFION® resins (from DuPont in Wilmington, Del.) can also be used as heterogeneous catalysts in neat form or filled with silica. In these embodiments, the resin-based catalyst is washed with water, and subsequently, an alcohol, such as methanol or ethanol, and then dried prior to use. Alternatively, the resin is not washed before its first use. In use, the heterogenous catalysts are added to a reaction mixture, thereby providing a nonvolatile source of acid protons for catalyzing the reactions. The heterogenous catalysts can be packed into columns and the reactions carried out therein. As the reagents elute through the column, the reaction is catalyzed and the eluted products are free of acid. In other embodiments, the heterogenous catalyst is slurried in a pot containing the reagents, the reaction is carried out, and the resulting reaction products filtered or distilled directly from the resin, leaving an acid-free material.

The amount of acid catalyst is about 2 to 20,000 parts per million (ppm), specifically about 10 to about 10,000 ppm, specifically about 20 to about 5000 ppm, and more specifically about 30 to about 2500 ppm, relative to the total weight of the reactants. In this case, the reactants are the sum of hydrocarbon polyol II and the 1.5 or more equivalents of a ketocarboxy acid III.

When camphor sulfonic acid is used as the acid catalyst to produce polyhydroxy ketal adduct I, it is used in amounts of about 5 to 5,000 parts per million (ppm), specifically about 10 to about 1000 ppm, specifically about 15 to about 800 ppm, and more specifically about 20 to about 600 ppm, relative to the total weight of the reactants. In this case, the reactants are the sum of hydrocarbon polyol II and the 1.5 or more equivalents of a ketocarboxy compound III.

The acid catalyst can be charged directly into the reactant mixture comprising the hydrocarbon polyol II and the ketocarboxy acid III or alternatively it can be diluted in water or one of the reactants prior to being charged into the reactant mixture. The acid catalyst can be diluted to about 0.01N to about 5N, specifically about 0.1N to about 4N, and more specifically about 0.5N to about 3N prior to introduction into the reactant mixture. The dilute acid catalyst can be continuously added to the reactant mixture throughout the course of the reaction or alternatively it can be added instantaneously to the reactant mixture in a single charge.

In an embodiment, in one method of manufacturing the polyketal adduct, the hydrocarbon polyol II and 1.5 or more equivalents of a ketocarboxy compound III are charged to the reactor. The reaction to produce the polyketal adduct can be conducted in either a batch reactor, a continuous reactor or in a semicontinuous reactor. It is desirable for the reactor to have heating, cooling, agitation, condensation, and distillation facilities.

In an embodiment, the batch reactor for producing the polyhydroxy ketal adducts can comprise a single continuous stirred tank reactor in fluid communication with a reboiler that is fitted with a distillation column. In another embodiment, the system (not shown) for producing the polyhydroxy ketal adduct I can comprise a single continuous stirred tank reactor that is fitted with a distillation column. The distillation column is used to remove excess reactants and to distill the water condensate from the reaction.

In a batch reactor, the reactants and catalyst are charged to the reactor in batches and the product is extracted from the reactor in batches only after the reaction has been completed to an extent of about 80% or more. While a batch reactor can be used to react the reactants under a variety of different conditions, it is desirable to use a batch reactor when the product is manufactured by introducing the acid catalyst into the reactor in one charge. An exemplary batch reactor is a stainless steel or Hastelloy-type reactor. An example of a batch reactor is a continuous stirred tank reactor. It is desirable for the batch reactor to be equipped with distillation facilities for further purification of the product. The reaction to produce the polyhydroxy ketal adduct I can be conducted in a single reactor or in plurality of batch reactors. In an embodiment, the esterification can be conducted in a batch reactor, while the ketalization can be conducted in the same or in a second batch reactor.

In a continuous reactor system the reactants are charged to a first reactor. When the conversion of reactants to products is measured to be greater than or equal to about 50%, a portion of the product mixture from the first reactor is subjected to additional finishing processes in a second reactor, while at the same time additional reactants and catalyst are continuously being charged to the first reactor to be converted into the polyhydroxy ketal adduct I. A continuous reactor system generally employs a plurality of reactors in series or in parallel so that various parts of the process can be conducted in different reactors simultaneously.

In an embodiment, the reactor comprises a plurality of reactors (e.g., a multistage reactor system) that are in fluid communication with one another in series or in parallel. The plurality of reactors are used to react the hydrocarbon polyol II with the ketocarboxy compound III, to recycle the reactants and to remove unwanted byproducts and impurities so as to obtain a polyhydroxy ketal adduct I that is stable and has a long shelf life. In an embodiment, a portion of the plurality of reactors can be used primarily to react reactants to manufacture the polyhydroxy ketal adduct I, while another portion of the plurality of reactors can be used primarily to isolate the ketocarboxylic ester IV and yet another portion of the plurality of reactors can be used to produce the polyhydroxy ketal adduct I or to remove the residual catalyst and other byproducts that can hamper the formation of a stable product that has good shelf stability.

In an exemplary embodiment, the esterification of the hydrocarbon polyol II with 1.5 or more equivalents of a ketocarboxy compound III to produce a ketocarboxylic ester IV is conducted in a batch reactor. In one method of manufacturing the polyketocarboxylic ester IV, a hydrocarbon polyol II and the ketocarboxy compound III are charged to the batch reactor along with the acid catalyst. The contents of the batch reactor are heated while being subjected to agitation. Volatile reactants or byproducts are collected in a condenser that is in fluid communication with the batch reactor. The ketocarboxylic ester IV can be isolated from unreacted reactants and other reaction byproducts prior to the ketalizing. In an embodiment, the ketocarboxylic ester IV is isolated via crystallization or distillation. In another embodiment, the ketocarboxylic ester IV is recrystallized prior to ketalizing.

In an embodiment, the batch reactor is heated to a temperature of about 110 to about 260° C., specifically about 150 to about 250° C., and specifically about 160 to about 240° C. to facilitate the esterification of the hydrocarbon polyol II by the ketocarboxy compound III. The esterification can be carried out under a blanket of an inert gas (e.g., argon, nitrogen, and the like) or alternatively can be carried out in a vacuum. The batch reactor can be subjected to a vacuum of about 5 to less than 760 torr, specifically about 10 to about 500 torr, more specifically about 10 to about 100 torr.

Upon completion of the esterification in the batch reactor, the reaction solution is cooled, which in some embodiments results in crystallization of the ketocarboxylic ester IV, particularly where each of the hydroxyl groups as been esterified. The crystalline ketocarboxylic ester IV can be washed in a first solvent to remove any contaminants. The washed ketocarboxylic ester IV can then be redissolved in a second solvent and recrystallized to produce a pure form of the ketocarboxylic ester IV. The first and the second solvent can be the same or different. In an embodiment, the first solvent is a protic solvent such as water, methanol, ethanol, or isopropanol, and the second solvent is water, methanol, ethanol, or isopropanol as well. In another embodiment, heating and cooling steps can be performed to conduct re-crystallization.

In still another embodiment upon completion of the esterification in the reactor, the ketocarboxylic ester IV is isolated from the reaction mixture by extraction and/or distillation. In either embodiment, the pure form of the ketocarboxylic ester IV can have a purity of greater than or equal to about 98%, specifically greater than or equal to about 99%, on a weight basis. The pure form of the ketocarboxylic ester IV wherein G is a $C_2$-$C_6$ alkylene, specifically a $C_2$-$C_4$ alkylene, more specifically ethylene, or 1,4-butylene, or 1,6-hexylene, more specifically still 1,4-butylene comprises white, shiny, spherical flakes or needle-shaped crystals.

The ketocarboxylic ester IV is then ketalized with the polyol V to produce the polyhydroxy ketal adduct I. During the ketalization, excess polyol V is removed from the polyhydroxy ketal adduct I by distillation. Thus, the ketocarboxylic ester IV, with or without purification as described above is then reacted with an excess of the polyol V in the presence of a second catalyst, which can the same or different as the first catalyst, in a ketalization reactor, which can be the same batch reactor or in a second batch reactor. The contents of the ketalization reactor are heated while being subjected to agitation to produce the polyhydroxy ketal adduct I. The contents of the ketalization reactor are heated to a temperature of about 60 to about 200° C., specifically about 70 to about 160° C., and specifically about 80 to about 140° C. to produce the polyhydroxy ketal adduct I. The ketalization reactor can be subjected to a vacuum of 5 to about 500 torr, specifically about 10 to about 100 torr.

Following the passage of a selected amount of time, the ketalization reactor is cooled and the reactants neutralized with a base. The reaction mixture is purified by filtration, extraction, or optionally by distillation to obtain the polyhydroxy ketal adduct I. In an embodiment, any unreacted ketocarboxylic acid IV can be removed from the reaction mixture by crystallization. In some embodiments, after cooling, the glycerol phase-separates from the reaction mixture. The excess glycerol can them be removed from the ketalization by simple decanting or centrifugation. The remaining reaction mixture can then be purified by suitable methods, including filtration, extraction, or distillation where appropriate. The distillation of the polyhydroxy ketal adduct I (or other desired products) can be carried out with wiped film evaporators, spinning film evaporators, rotary evaporators, falling film evaporators and other similar equipment.

Use of the foregoing processes can produce the polyhydroxy ketal adduct I containing less than or equal to about 0.001 to about 10 ppm sulfur-containing acid impurities, specifically about 0.002 to about 5 ppm sulfur-containing acid impurities, based on the total weight of the composition. In a particularly advantageous feature, such levels are obtainable without distillation of the polyhydroxy ketal adduct I after synthesis.

Alternatively, or in addition, the polyhydroxy ketal adduct I can contain less than or equal to about 10 parts per million (ppm), specifically less than or equal to about 5 ppm, more specifically less than or equal to about 2 ppm, or less than or equal to about 1 ppm, or less than or equal to about 0.5 part per million of a total content of transition metals. In an embodiment, essentially no transition metal is present. In another embodiment, a content of the transition metal is 0 to 10 ppm, specifically 0.1 to 5 ppm, more specifically 0.5 to 2 ppm. In a specific embodiment, the polyhydroxy ketal adduct I contains less than 1 ppm of a total content of cobalt, nickel, tin, antimony, titanium, zirconium, or aluminum. In a particularly advantageous feature, such low quantities of transition metal impurities are obtainable without purification, e.g., without distillation of the polyhydroxy ketal adduct I after synthesis.

The polyhydroxy ketal adduct I can further comprise an intermediate e.g., at least one of the ketocarboxylic ester IV, or various byproducts of the reactions. For example, the polyhydroxy ketal adduct I can further comprise one or more of the ketocarboxylic ester (Iv),

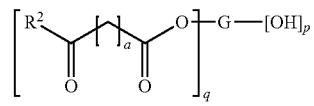

a hydroxy ketoester VII,

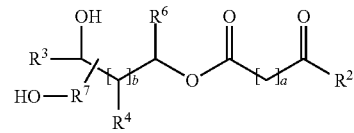

or a hydroxy ketal ester VIII

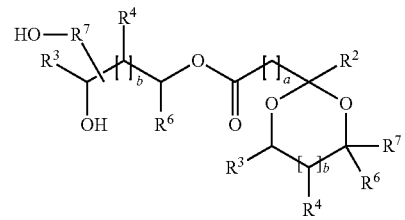

or a combination comprising at least one of the foregoing, wherein G, $R^2$, each $R^3$, $R^4$, $R^6$, $R^7$, a, b, p, and q are a described in polyhydroxyketal I above. Other regioisomers of the hydroxy ketoester VII and hydroxyketal ester VIII (where esterification occurs at one of the other two hydroxyl groups of polyol V).

In another specific embodiment, the intermediate or byproduct can be the ketocarboxylic ester IVa,

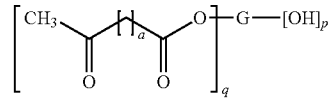

the hydroxy ketoester VIIa,

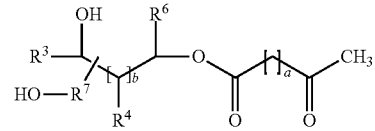

or the hydroxy ketal ester VIIIa,

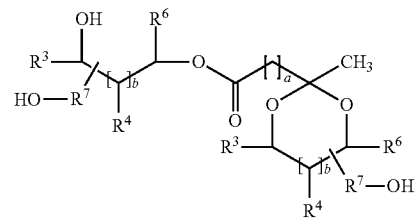

or a combination comprising at least one of the foregoing, wherein G each $R^3$, $R^4$, $R^6$, $R^7$, a, b, p, and q are a described in polyhydroxyketal Ib above. Other regioisomers of the hydroxy ketoester VII and hydroxyketal ester VIII (where esterification occurs at one of the other two hydroxyl groups of polyol V).

In another specific embodiment, the intermediate or byproduct can be the ketocarboxylic ester IVa, a hydroxy ketoester VIIb,

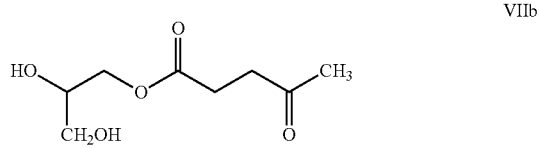

VIIb a hydroxy ketal ester VIIIb,

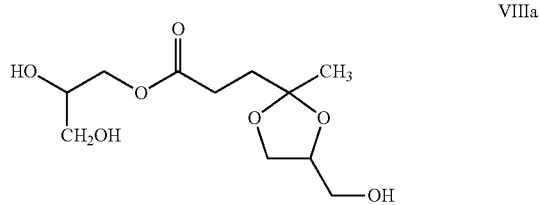 [SMILES: CC1(CCC(=O)OCC(O)CO)OCC(CO)O1]

VIIIa or a combination comprising at least one of the foregoing. Other regioisomers of the hydroxy ketoester VII and hydroxyketal ester VIII (where esterification occurs at one of the other two hydroxyl groups of glycerol).

In any of the foregoing embodiments the polyhydroxy ketal adduct I, each of the intermediates or byproducts, e.g., the ketocarboxylic ester IV, hydroxy ketoester VII, and hydroxy ketal ester VIII, can independently be present in an amount of 0-10 wt %, specifically 0.1-7 wt %, more specifically 0.5-5 wt %, based on a total weight of the composition. In an embodiment, the total amount of byproducts, e.g., a total amount of the ketocarboxylic ester IV, hydroxy ketoester VII, and hydroxy ketal ester VIII, is 0-10 wt %, specifically 0.1-7 wt %, more specifically 0.5-5 wt %, based on the total weight of the polyketal adduct composition.

The polyhydroxy ketal adduct I can have a low yellowness index (YI), for example a YI of less than or equal to about 200, specifically less than or equal to about 150, and more specifically less than or equal to about 100 as measured by ASTM E313. In a specific embodiment, the ketal adduct I can have a YI of less than or equal to about 100, specifically less than or equal to about 50, and more specifically less than or equal to about 10 as measured by ASTM E313. In a particularly advantageous feature, such levels are obtainable without distillation of the polyhydroxy ketal adduct I after synthesis.

The polyketal adduct I can be used as an intermediate for the manufacture of other compounds, or as a component or additive with a variety of organic polymers to form a polymer composition. In an embodiment, the polyhydroxy ketal adduct I can be converted into a polymer that is used as a thermoplastic, a thermoset, a coating, plasticizer, a toughener, a surfactant, a barrier layer compound, an interfacial modifier, a compatibilizer, a foam, or a phase transfer compound.

For example, the polyhydroxy ketal adduct I can be advantageously reacted with amino resins to form, for example coatings and adhesive binders. The reaction is catalyzed by acid catalysts, for example aromatic sulfonic acid catalysts. Amino resins are reaction products of certain amines and ureas with formaldehyde and one of more aliphatic alcohols. The amino resins can be monomeric or oligomeric. Examples of amino resins are melamine-formaldehyde resins, urea-formaldehyde resins, benzoguanamine-formaldehyde resins, and glycoluril-formaldehyde resins. Other exemplary amino resins are methylated melamine-formaldehyde resins, butylated melamine-formaldehyde resins, and methylated urea-formaldehyde resins. The resins are generally etherified with an alcohol selected from methanol, ethanol, propanol, n-butanol, or i-butanol. Depending upon the type and equivalents of alcohol present, the amino resin can be water-soluble or soluble in organic solvents.

The polyhydroxy ketal adduct I can be used to prepare polyurethanes directly by reaction with a polyisocyanate, or to prepare isocyanate functional prepolymers by contacting the polyhydroxy ketal adduct I with an organic polyisocyanate to form a polyisocyanate-capped prepolymer. Conditions for achieving either product as desired are known in the art.

Non-limiting examples of organic polyisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl) methane, 2,4'-dicyclohexyl-methane diisocyanate, 4,4'-dicyclohexyl-methane diisocyanate, 1,3-bis-(isocyanatomethyl)-cyclohexane, 1,4-bis-(isocyanatomethyl)-cyclohexane, bis-(4-isocyanato-3-methyl-cyclohexyl)methane, a, a, α',α'-tetramethyl-1,3-xylylene diisocyanate, a, a, α', α'-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2, 2'-diphenylmethane diisocyanate, 2,4'-diphenylmethane diisocyanate, 4,4'-diphenylmethane diisocyanate, or 1,5-diisocyanato naphthalene. A combination comprising at least one of the foregoing can be used. The organic polyisocyanate can also be in the form of a polyisocyanate adduct. The polyisocyanate adducts include those containing isocyanurate, uretdione, biuret, urethane, allophanate, carbodiimide and/or oxadiazinetrione groups. Examples of polyisocyanate cross-linkers used in coatings and adhesives for outdoor applications where exterior durability is required are bis(4-isocyanatocyclohexyl)methane, the isocyanurate trimers of 1,6-hexanediisocyanate and isophorone diisocyanate, the biuret of 1,6-hexanediisocyanate, and the uretdione of 1,6-hexanediisocyanate. Specific polyisocyanates include diphenylmethane-4,4'-diisocyanate, the reaction product of trimethylolpropane with toluene diisocyanate, and the isocyanurate trimer of toluene diisocyanate.

Preparing the polyurethane or the polyisocyanate prepolymer can be effected by contacting the polyhydroxy ketal adduct I or other polyol, or a combination thereof, and the appropriate stoichiometry of a polyisocyanate and causing a reaction to occur by heating and/or with a catalyst to accelerate the reaction. Non-limiting examples of catalysts for making the polyurethanes and polyisocyanate compounds include tin catalysts such as dibutyl tin dilaurate, and tertiary amines such as 1,4-diazabicyclo[2.2.2]octane (DABCO™, TED), and the like. The reaction can be carried out in the presence of an inert solvent, which can optionally be removed at the end of the reaction by distillation or extraction.

Non-limiting examples of polyols include 1,2-ethanediol (ethylene glycol), 1,2-propanediol (propylene glycol), 1,3-propanediol, 2,2-dimethyl-1,3-propanediol(neopentyl glycol), 2-butyl-2-ethyl-1,3-propanediol, 3-mercaptopropane-1,2-diol (thioglycerol), dithiothreitol, 1,2-butanediol, 1,3-butanediol, 1,4-butanediol, 2,3-butanediol, 1,5-pentanediol, 3-methyl-1,5-pentanediol, 1,6-hexanediol, 2-ethyl-1,3-hexanediol, cyclohexane-1,2-diol, cyclohexane-1,4-diol, 1,4-dimethylolcyclohexane, 1,4-dioxane-2,3-diol, 3-butene-1,2-diol, 4-butenediol, 2,3-dibromobutene-1,4-diol, 1,8-octanediol, 1,10-decanediol, 1,12-dodecanediol, benzene-1,2-diol (catechol), 3-chlorocatechol, indane-1,2-diol, tartaric acid, and 2,3-dihydroxyisovaleric acid, diethylene glycol (DEG), Methylene glycol, tetraethylene glycol, dipropylene glycol, tripropylene glycol, tetrapropylene glycol, xylene glycol, 1,3-benzenediol (resorcinol), 1,4-benzenediol (hydroquinone), o-, m-, or p-benzene dimethanol, o-, m-, or p-glycol phthalates, o-, m-, or p-bis-1,2-ethylene glycol phthalates, o-, m-, or p-bis-1,2-propylene glycol phthalates, o-, m-, or p-bis-1,3-propylene glycol phthalates, diols prepared by hydrogenation of dimer fatty acids, hydrogenated bisphenol A, hydrogenated bisphenol F, propoxylated bisphenol A, isosorbide, 2-butyne-1,4-diol, 3-hexyne-3,5-diol (SURFYNOL® 82, available from Air Products of Allentown, Pa.) and other alkyne-based polyol products marketed under the SURFYNOL® brand name by Air Products of Allentown, Pa., and polymeric polyols such as polyether polyols based on ethylene glycol, for example CARBOWAX® polyethylene glycols (available from The Dow® Chemical Company of Midland, Mich.), polyether diols and polyols based on propylene glycol or combinations of ethylene glycol and propylene glycol, such as those sold by the Dow® Chemical Company of Midland, Mich., and polyether glycols such as those produced by the INVISTA™ Company of Wichita, Kans. under the trade name TERETHANE®; polycarbonatediols of varying molecular weights, such as L467m, L600m, and L565m, available from Asahi Kasei Corporation (Tokyo, Japan); polyols based on hydroxylated vegetable oils, such as those sold under the trade name BiOH®, available from the Cargill Company of Wayzata, Minn.; hydroxyl-terminated polybutadienes, such as HTPB R45M, sold by Aerocon Systems of San Jose, Calif., polyols produced by the Everchem Company of Media, Pa., or the Maskimi Polyol Sdn. Bhd. of Kajang, Selango Darul Ehsan, Malaysia, and the polyols employed in the Union Carbide Company (South Charleston, W. Va.) publication by Carey, Mass. et al., "Rapid Method for Measuring the Hydroxyl Content of Polyurethane Polyols" (published on the internet at http://www.polyurethane.org/s_api/doc_paper.asp?CE)=1044&DID=4060, accessed on Nov. 9, 2010).

Various polyurethane polymers can be prepared using the prepolymer and the polyurethane can be used to manufacture a wide variety of polyurethane goods, which can be solid, foams, or viscous liquids, rigid or flexible, thermoset or thermoplastic. The foams can be rigid, soft, or viscoelastic (i.e., a "memory" foam that returns to its original shape after deformation. Depending on the specific polymer composition, they can be cast, extruded, or otherwise shaped in a variety of forms needed to manufacture finished polymer goods, including films. The polyurethanes can contain various additives known in the art, such flame retardants, surfactants, catalysts, blowing agents, water, organic or inorganic fillers, pigments, stabilizers, anti-oxidants, and lubricants. The polyurethanes disclosed herein are made with use of low-cost renewable monomers to provide the predominant part of the weight of the resulting polymers, thereby offering a cost advantage when compared to the known in the art polyurethanes made predominantly or exclusively with use of non-renewable petroleum- or coal-derived monomers.

In one embodiment, the polyhydroxy ketal adduct I is part of a polyol formulation comprising the polyhydroxy ketal adduct I, and other optional components, including water, surfactants, catalysts, blowing agents and flame retardants.

The polyurethanes are also recyclable at the monomer level. If so desired, at the end of their useful life, the polyurethane polymers can be treated by a trans-esterification reaction, to allow for the decomposition of the polymers and the formation of one or more predecessor monomers which can be recovered, purified and re-used.

The polyhydroxy ketal adduct I can also be used to prepare polycarbonates. In general, any of the techniques found in the literature that are useful for making polycarbonates are also useful to make the polycarbonates. In some embodiments, a polyhydroxy ketal adduct I compound is reacted with phosgene. In one such embodiment, the polyhydroxy ketal adduct I is reacted with aqueous sodium hydroxide to form the corresponding sodium salt. The aqueous phase is then contacted with an immiscible organic phase containing phosgene. A linear polymer is formed, in embodiments, at the interface between the aqueous and organic phases.

In some such embodiments, the sodium cation is exchanged for a more organic miscible cation, such as tetrabutylammonium and the like, prior to commencing the interfacial reaction. Tetraalkylammonium cations are sometimes referred to in the literature as phase transfer catalysts, and have been observed to cause increased rates of interfacial reaction by increasing the miscibility of the salt in the organic phase. In some embodiments, employing a phase transfer catalyst with the polyhydroxy ketal adduct I salts increases the rate of interfacial reaction to form the polycarbonates. In other embodiments, the polyhydroxy ketal adduct I structures and their sodium salts possess sufficient organic miscibility that the use of phase transfer catalyst is not required to reach satisfactory rates of reaction.

In some embodiments, the polycarbonates are synthesized by the reaction of a polyhydroxy ketal adduct I with a diester of carbonic acid having the general structure

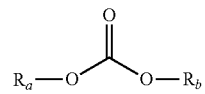

wherein $R_a$ and $R_b$ can be the same or different and represent optionally substituted aliphatic, aryl-aliphatic or aromatic hydrocarbon radicals having 1 to 16 carbon atoms. $R_a$ and $R_b$ can further contain heteroatoms, such as halogen, nitrogen, silicon, sulfur, phosphorus, or oxygen. Nonlimiting examples of dialkyl carbonates include dimethyl carbonate, diethyl carbonate, di-n-propyl carbonate, di-n-butyl carbonate, di-isobutyl carbonate, bis(2-bromoethyl) carbonate, bis(2,2,2-trichloroethyl) carbonate, ethyl (4-methylphenyl) carbonate, diphenyl carbonate, bis(2-methoxyphenyl)

carbonate, bis(4-nitrophenyl) carbonate, dinaphthalen-1-yl carbonate, dibenzyl carbonate, and the like.

In embodiments, carbonate diesters are used to synthesize the polycarbonates using any of the known techniques in the literature for making polycarbonates from diols or higher polyols and dialkyl carbonates or diarylcarbonates. For example, Moethrath et al., U.S. Patent Publication No. 2003/0204042 teach the synthesis of high molecular weight aliphatic polycarbonates employing a two-stage process wherein a low molecular weight aliphatic polycarbonate is formed, followed by condensation of the low molecular weight adduct with a diaryl carbonate to give a high molecular weight final product. In another example, Schnell et al., German Patent No. DE 1 031 512 disclose the synthesis of high molecular weight aliphatic polycarbonates employing diethyl carbonate and alkali catalysts in conjunction with a base-binding compound, such a phenyl chloroformate. The described methods are also useful to form the polycarbonates.

In some embodiments, the polycarbonates have 1 and about 30 units, corresponding to molecular weights of about 500 to about 30,000 g/mol, depending on the molecular weight of polyhydroxy ketal adduct I. In various embodiments, the polycarbonates have a broad range of available properties due to the range of polyhydroxy ketal adducts I available from the methods described herein. In some embodiments, the polycarbonates possess good toughness and thermal stability. In some embodiments the polycarbonates are transparent to visible light and possess good clarity and low color, e.g., are "water white." In some embodiments, the combination of toughness, thermal stability, and transparency make the polycarbonates desirable for a wide range of applications.

The polycarbonates are synthesized, in preferred embodiments, from biomass-based feedstocks. The glycerol and 1,1,1-trimethylolpropane ketals of levulinic and pyruvic acid, and esters thereof, are derivable or potentially derivable from biomass sources and do not require the use of petroleum based feedstocks. Also, carbonate precursors such as dialkylcarbonates are based in part on non-petroleum sources. In embodiments, at least 20% by weight the polycarbonates are biomass based. In other embodiments, between about 20% and 90% by weight the polycarbonates are biomass based. In other embodiments, between about 40% and 75% by weight the polycarbonates are biomass based.

In some embodiments, the polycarbonates are terminated by two hydroxyl endgroups. Such compounds I are useful as diols for use in polyurethane synthesis. In some such embodiments, polycarbonates having values of γ of 1 to about 30 and two hydroxyl endgroups are, in embodiments, useful as feedstocks for synthesis of polyurethanes. Such polycarbonate I diols are synthesized, in some embodiments, by controlling stoichiometry of the polycarbonate polymerization in order to provide hydroxy ketal ester functionality or hydroxyalkyl at the ends of the polycarbonate. Polycarbonates having hydroxyl endgroups are, in embodiments, reacted with one or more polyisocyanates to form a polyurethane that is a poly(carbonate urethane). Poly(carbonate urethane)s are synthesized using any of the known techniques in the literature that are employed to make polyurethanes from polyols and employ known polyisocyanates in the reactions. In some such embodiments, techniques used to form the poly(carbonate urethane)s are those outlined in Moore et al., *Novel Co-Polymer Polycarbonate Diols for Polyurethane Elastomer Applications*, Proceedings of the Polyurethanes Expo 2003, Oct. 1-3, 2003 (® 2003, American Chemistry Council).

The polyhydroxy ketal adduct I can also be used to prepare copolyesters. These materials can be used for developing products having physical properties useful for replacing present fully petrochemical-based polymers for thermoplastics, coatings, elastomers, adhesives, sealants, and other industrial applications of organic polymers. Due to the biocompatibility of the major products formed on breakdown by acidic hydrolysis, these materials will be useful for fabrication or coating of medical devices or as the matrix materials for controlled release of pharmaceutical or agrochemical actives.

The copolyesters are prepared by the condensation of a diacid and polyhydroxy ketal adduct I, optionally with an additional diol. The diol can be as disclosed above. The copolymerization is accomplished by esterification or transesterification of ketal acids and esters thereof by employing standard techniques of polyesterification, which can be similar to the reaction conditions employed to form the ketocarboxylic ester IV. The stoichiometry of the copolymerization is selected according to total hydroxyl number and acid number to obtain the desired degree of polymerization.

Non-limiting examples of diacids include aliphatic, cycloaliphatic or aromatic dicarboxylic acids, for example, succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioic acid, dimerized fatty acids, or hydrogenated dimerized fatty acids. The methyl, ethyl, propyl, butyl or phenyl esters of the acids listed above are substitutes for the diacid component, as well as acid anhydrides (such as o-phthalic, maleic or succinic acid anhydride). A combination comprising at least one of the foregoing can be used The polyhydroxyketal ester adduct can also be combined with a polymer to provide a polymer composition, for example a plasticized polymer composition. The polymer can be a thermoplastic. In an embodiment, the polymer is a polylactic acid, a polyvinylchloride, a polyacetal, a polyolefin, a polysiloxane, a polyacrylic, a polycarbonate, a polystyrene, a polyester, a polyamide, a polyamideimide, a polyarylate, a polyarylsulfone, a polyethersulfone, a polyphenylene sulfide, a polyvinyl chloride, a polysulfone, a polyimide, a polyetherimide, a polytetrafluoroethylene, a polyetherketone, a polyether etherketone, a polyether ketone ketone, a polybenzoxazole, a polyphthalide, a polyacetal, a polyanhydride, a polyvinyl ether, a polyvinyl thioether, a polyvinyl alcohol, a polyvinyl ketone, a polyvinyl halide, a polyvinyl nitrile, a polyvinyl ester, a polysulfonate, a polysulfide, a polythioester, a polysulfone, a polysulfonamide, a polyurea, a polyphosphazene, a polysilazane, or a combination comprising at least one of the foregoing organic polymers.

In an embodiment, the composition can further comprise an additive, where the additive is an antioxidant, an antiozonant, a thermal stabilizer, a mold release agent, a dye, a pigment, an antibacterial, a flavorant, a fragrance molecule, an aroma compound, an alkalizing agent, a pH buffer, a conditioning agent, a chelant, a solvent, a surfactant, an emulsifying agent, a blowing agent, a foam stabilizer, a hydrotrope, a solubilizing agent, a suspending agents, a humectant, an accelerator, a ultraviolet light absorber, or a combination comprising at least one of the foregoing additives.

The polyketal adduct can be added to the organic polymer in amounts of about 0.1 wt % to about 90 wt %, specifically about 4 wt % to about 70 wt %, and more specifically about 40 to 60 wt %, based on the total weight of the polymer composition.

In an embodiment, in one method of manufacturing a polymer composition, the polyhydroxy ketal adduct I is blended with an organic polymer. The blending generally involves melt blending, which comprises melting the thermoplastic polymer and dispersing the polyhydroxy ketal adduct I into the molten thermoplastic polymer. Pre-blending of the thermoplastic polymer and the polyhydroxy ketal adduct I can be conducted prior to the melt blending.

In an embodiment, the compositions can be prepared by pre-blending the thermoplastic polymer and the polyhydroxy ketal adduct I prior to being fed into a melt blending device, although such pre-blending cannot always be desired. The pre-blending can be carried out in a mixer such as, for example, a drum mixer, ribbon mixer, vertical spiral mixer, Muller mixer, sigma mixer, chaotic mixer, static mixer, and the like. Pre-blending is generally carried out at room temperature.

The melt blending can result in the formation of an intermediate product such as, for example, pellets or briquettes that can be subsequently manufactured into an article or it can result in the direct formation of articles via a molding process.

Melt blending of the composition involves the use of shear force, extensional force, compressive force, ultrasonic energy, electromagnetic energy, thermal energy or combinations comprising at least one of the foregoing forces or forms of energy, and is conducted in processing equipment wherein the aforementioned forces or forms of energy are exerted by a single screw, multiple screws, intermeshing co-rotating or counter rotating screws, non-intermeshing co-rotating or counter rotating screws, reciprocating screws, screws with pins, screws with screens, barrels with pins, rolls, rams, helical rotors, or combinations comprising at least one of the foregoing.

Melt blending involving the aforementioned forces can be conducted in machines such as single or multiple screw extruders, Buss kneaders, Henschel mixers, helicones, Ross mixers, Banbury, roll mills, molding machines such as injection molding machines, vacuum forming machines, blow molding machines, or the like, or a combination comprising at least one of the foregoing machines. After melt blending, an intermediate product such as pellets or briquettes can be formed, which can then be used for subsequent manufacture into an article, for example by molding. Alternatively, the melt-blended composition can be used in the direct formation of articles via casting to form a layer or molding into an article having a desired shape. Molding can be conducted by compression molding, injection molding, vacuum forming, extrusion, blow molding, or the like.

The polymer composition is useful to form a variety of articles. An "article" as used herein is an item with a discrete shape, such as a tube, a film, a sheet, or a fiber, that incorporates one or more compositions of the disclosure; in some embodiments, the article can have its origin in a composition that undergoes a transformation, such as solidification or evaporation of one or more solvents, to result in the final article. In some embodiments, an article is substantially formed from a polymer composition; in other embodiments, the polymer composition forms only one part, such as one layer, of an article.

The article is, in some embodiments, a casing, a pipe, a cable, a wire sheathing, a fiber, a woven fabric, a nonwoven fabric, a film, a window profile, a floor covering, a wall base, an automotive item, a medical item, a toy, a packaging container, a screw closure or stopper adapted for a bottle, a gasket, a sealing compound, a film, a synthetic leather item, an adhesive tape backing, or an item of clothing. In some embodiments, the casing is a casing for an electrical device. In some embodiments, the medical item is medical tubing or a medical bag. In some embodiments, the film is a roofing film, a composite film, a film for laminated safety glass, or a packaging film. In some embodiments, the packaging container is a food or drink container. In some embodiments, the sealing compound is for sealed glazing. In some embodiments, the automotive item is seat upholstery, an instrument panel, an arm rest, a head support, a gear shift dust cover, a seat spline, a sound-deadening panel, an impact absorbing article, a window seal, a landau top, a sealant, a truck tarpaulin, a door panel, a cover for a console and glove compartment, a trim laminating film, a floor mat, a wire insulation, a side body molding, an underbody coating, a grommet, or a gasket.

The polyhydroxy ketal adduct I can be used in a variety of personal care products such as shampoos, lotions, shaving creams, deodorants, and the like.

In another embodiment, the polyhydroxy ketal adduct I find use in a variety of coating compositions, for example paints, inks, or water-borne coating compositions. Depending on the end use of the composition, the ketal adducts can function as a polymer binder, or a condensation reactive product. In an embodiment, the ketal adducts also function as a plasticizer, increasing the flexibility of the compositions. In a highly advantageous feature, selection of the specific G, $R^1$, $R^2$, $R^3$, $R^4$, $R^6$, and $R^7$ groups, and a and b in the ketal adducts I allows the chemical and physical properties of the ketal adducts to be adjusted to achieve the desired combination of properties, for example film flexibility or mechanical strength.

Thus, in an embodiment, a coating composition comprises a polymer binder resulting from the reaction of the polyhydroxy ketal adduct I with another component, and a carrier, such as water or an organic solvent.

The type of polymer binder can be selected from a wide variety of polymers known in the art of coating compositions, specifically paint compositions, and include, for example, polyurethanes, epoxies and epoxy esters. In a specific embodiment, the binder is a polyurethane, for example an aliphatic polyurethane. The various types of polymer binders may be made water-reducible by neutralizing residual carboxylic acid groups attached to the polymer backbone with a base, for example an organic amine, ammonium hydroxide, or other base.

The polymer binder can be thermosetting, in which case any curing agent utilized for each polymer binder will depend on the nature of the particular polymer and its curing mechanism. Blocked isocyanate crosslinking agents are also known in the art. Catalysts can also be used to promote the curing reaction, such as peroxides. In addition to catalysts, promoters and activators for promoting the curing reaction can be used.

Some polymer binders, e.g., curable polyurethane binders, include two components: an active hydrogen-containing component (e.g., the polyhydroxy ketal adduct I) and an optional carrier component, which can include water or an organic solvent in one part and a polyisocyanate and optional carrier in another part.

Epoxy binders include derivatives of diglycidyl ether/bisphenol compounds such as bisphenol A (DGEBA), i.e., derivatives of polyether diepoxides that are obtained from the polymeric adduction of bisphenols with the diglycidyl ether of the bisphenol. The epoxies can be rendered water-soluble by reacting them with phosphoric acid and then neutralizing the resulting, acidic, ester, and glycol-comprising reaction products with a base. If the base is a fugitive base, such as ammonia or a volatile amine, the water-thinned, neutralized polymer can be converted to a water-insensitive, high performance thermoset polymer binder by evaporating the water, heating to disrupt the ammonium salt groups and drive off the ammonia (or amine), and curing. Polyhydroxy ketal adduct I can function as a curing agent capable of reacting with the epoxy. Epoxy binders can also be made with a surfactant to aid in dispersion. In some cases, the surfactant can have reactive groups so that the surfactant is chemically incorporated into the polymer system.

The polymer binder resulting from the reaction of the polyhydroxy ketal adduct I can be present in the carrier completely dissolved, i.e., in the form of a solution, in the form of aggregates, or a dispersion, and can include about 5 to about 85 weight percent (wt. %) solids, specifically about 10 to about 75 wt. % solids, specifically about 30 to about 65 wt. % solids (i.e., the weight percentage of the polymer binder based on the total weight of the coating composition). As used herein, "solids" refers to the 100% binder in whatever form, such as a solid or liquid. The polymer binder can be present in a wide variety of particle sizes, for example a mean polymer binder particle size from about 10 to about 1,000 nanometers (nm), specifically about 50 to about 800 nm. The particle size distribution can be mono-modal or multimodal, for example bimodal.

The polymeric binder comprising the reaction product of the polyhydroxy ketal adduct I is present in the coating composition in an amount effective for its purpose, i.e., thickness of a film, hardness of the film, abrasion resistance and the like. Such amounts can be determined by one of ordinary skill in the art, and can be for example, from about 2 to about 65 wt. %, or 5 to about 50 wt. %, specifically about 20 to about 50 wt. % based on the total weight of the coating compositions. The balance of the coating compositions is carrier, and other optional additives, including cosolvents known in the art.

A method of preparing a coating composition comprises combining a polymer binder comprising the reaction product of polyhydroxy ketal adduct I, a carrier, such as an aqueous phase (i.e., water and any cosolvents if present) or an organic solvent system, and any additives, if present, to form a coating composition. The components can be added in any suitable order to provide the coating composition.

In a specific embodiment, the polyhydroxy ketal adduct I is used in a water-borne or solvent-borne paint compositions, stain composition, or clear-coat compositions, Thus, in an embodiment, a paint, stain, or clear-coat composition comprises the polymer binder composition comprising the reaction product of polyhydroxy ketal adduct I, a carrier and optionally a pigment. When the polymer binder is thermosetting, the composition includes the polyhydroxy ketal adduct I and can comprise one or more of a catalyst, initiator, or promoter, if used.

A pigment can be present in the paint or stain composition. The term "pigment" as used herein includes non-film-forming solids such as extenders and fillers, for example an inorganic pigment aluminum oxide, barites (barium sulfate), CaCO3 (in both ground and precipitated forms), clay (aluminum silicate), chromium oxide, cobalt oxide, iron oxides, magnesium oxide, potassium oxide, silicon dioxide, talc (magnesium silicate), TiO2 (in both anastase and rutile forms), zinc oxide, zinc sulfite, an organic pigment such as solid (high Tg) organic latex particles added to modify hardness or (as in the case of hollow latex particles) to replace TiO2, carbon black, and a combination comprising at least one of the foregoing. Representative combinations include blends of metal oxides such as those sold under the marks Minex® (oxides of silicon, aluminum, sodium and potassium commercially available from Unimin Specialty Minerals), Celites® (aluminum oxide and silicon dioxide commercially available from Celite Company), Atomites® (commercially available from English China Clay International), and Attagels® (commercially available from Engelhard). Specifically, the pigment includes $TiO_2$, $CaCO_3$, or clay.

Generally, the mean particle sizes of the pigments are about 0.01 to about 50 micrometers. For example, the TiO2 particles used in the aqueous coating composition typically have a mean particle size from about 0.15 to about 0.40 micrometers. The pigment can be added to the aqueous coating composition as a powder or in slurry form.

A dye can be present in the paint or stain composition, in addition to or instead of a pigment. The term "dye" as used herein includes organic compounds generally soluble in the compositions, and that impart color to the compositions.

The paint, stain, or clear-coat composition can contain additional additives, as known in the art, to modify the characteristics of the composition, provided that the additives do not significantly adversely affect the desired properties of the paint, stain, or clear-coat, for example, viscosity, drying time, or other characteristic. These additives can include a plasticizer, drying retarder, dispersant, surfactant or wetting agent, rheology modifier, defoamer, thickener, biocide, mildewcide, colorant, wax, perfume, pH adjuster, or cosolvent. The additives are present in the amount ordinarily used in paint, stain, or clear-coat compositions. In an embodiment, the paint, stain, or clear-coat composition consists essentially of a polymeric binder comprising the reaction product of polyhydroxy ketal adduct I, a carrier, an optional pigment, and an optional dye. As used herein, the phrase "consists essentially of" encompasses the polymeric binder, carrier, optional pigment, and optionally one or more of the additives defined herein, but excludes any additive that significantly adversely affects the desired properties of the composition or the dried coating derived therefrom.

The polymer binder comprising the reaction product of polyhydroxy ketal adduct I can be present in the paint composition in an amount from about 2 to about 60 wt. %, and more specifically about 4 to about 40 wt. % of the paint composition, based on the dry weight of the polymer binder. When present, the pigment can be used in the paint composition in an amount from about 2 to about 50 wt. %, specifically about 5 to about 40 wt. % of the total solids in the paint composition.

The polymer binder comprising the reaction product of polyhydroxy ketal adduct I can be present in the stain composition in an amount from about 0.1 to about 50 wt. %, and more specifically about 0.5 to about 30 wt. % of the stain composition, based on the dry weight of the polymer binder. When present, the pigment or dye can be used in the stain composition in an amount from about 0.1 to about 40 wt. %, specifically about 0.5 to about 30 wt. % of the total solids in the stain composition. When present, the dye can be used in the paint or stain composition in an amount from about 0.001 to about 10 wt. %, specifically about 0.005 to about 5 wt. % of the total solids in the paint or stain composition.

The polyhydroxy ketal adduct I can be present in an amount from about 1 to about 90 wt. %, specifically about 10 to about 85 wt. %, more specifically about 10 to about 50 wt. %, and still more specifically about 10 to about 30 wt. %, based on the dry weight of the polymer binder.

The paint composition can include about 5 to about 85 wt. % and more specifically about 35 to about 80 wt. % carrier, i.e., the total solids content of the paint composition can be about 15 to about 95 wt. %, more specifically, about 20 to about 65 wt. % of the total composition. The compositions can be formulated such that the hardened (dried) coatings comprise at least about 2 to about 98 volume % (vol. %) polymer solids comprising the reaction product of polyhydroxy ketal adduct I, and about 2 to about 98 vol. % of non-polymeric solids in the form of pigments or a combination of a pigment and a dye, together with other additives (if present).

The water-reducible stain composition can includes about 10 to about 95 wt. % and more specifically about 25 to about 90 wt. % water, i.e., the total solids content of the water-reducible stain composition can be about 5 to about 75 wt. %, more specifically, about 10 to about 75 wt. % of the total composition. The stain compositions are typically formulated such that the hardened (dried) coatings comprise at least about 1 vol. %, for example about 5 to about 98 vol. % polymer solids comprising the polyhydroxy ketal adduct I, and about 0.1 to about 99 vol. % of non-polymeric solids in the form of pigments and/or dyes, and other additives (if present). A wood stain coating can penetrate the wood substrate to some degree.

The clear-coating composition can include about 10 to about 95 wt. % and more specifically about 25 to about 90 wt. % carrier, i.e., the total solids content of the clear-coating composition can be about 5 to about 75 wt. %, more specifically, about 10 to about 75 wt. % of the total composition. The compositions are typically formulated such that the hardened (dried) clear-coatings comprise at least about 1 vol. % polymer solids, for example about 1 to about 100 vol. % polymer solids comprising the reaction product of polyhydroxy ketal adduct I, and 0 to about 10 vol. % of non-polymeric solids. For example, in clear-coat compositions certain additives (e.g., calcium carbonate, talc, or silica) can be used that do not impart color, but rather serve primarily to reduce formulation cost, modify gloss levels, or the like.

In an embodiment, a method of preparing a paint, stain, or clear-coating composition comprises combining the polymer binder comprising the reaction product of polyhydroxy ketal adduct I, the pigment (if used), carrier, and any optional additives to form a composition. The components can be added in any suitable order to provide the composition.

In another embodiment, the components of the coating composition, e.g., a paint, stain, or clear-coat composition, are provided in two parts that are combined immediately prior to use. For example, a first part of an epoxy coating composition includes an epoxy dispersion and a second part includes the polyhydroxy ketal adduct I. The parts are mixed in a predetermined ratio, optionally with a catalyst, to provide the epoxy system.

In another embodiment, the components of the coating composition, e.g., a paint, stain, or clear-coat polyurethane composition, are provided in two parts that are combined immediately prior to use. The polyhydroxy ketal adduct I can be combined in a first component that is mixed together with a second component containing an isocyanate. In another embodiment, a first polyol component is mixed together with a second component comprising an isocyanate-tipped prepolymer comprising the reaction product of polyhydroxy ketal adduct I. The parts are mixed in a predetermined ratio to provide the polyurethane system. In a moisture-cured, one-component system, the polyhydroxy ketal adduct I is incorporated into a isocyanate-tipped prepolymer that is coated onto a substrate and cured by reaction with moisture in the air.

In another exemplary embodiment, a method of use, that is, coating a substrate with the paint, stain, or clear-coat composition is described. The method comprises contacting a surface of the substrate with the paint, stain, or clear-coat composition to form a film; and drying the film to harden the film. The composition can at least partially impregnate the substrate after contacting. The film can further optionally be cured.

The substrate can be a wide variety of materials, including but not limited to, paper, wood, concrete, metal, glass, textiles, ceramics, plastics, plaster, roofing substrates such as asphaltic coatings, roofing felts, foamed polyurethane insulation, polymer roof membranes, and masonry substrates such as brick, cinderblock, and cementitious layers, including EIFS systems (synthetic stucco made from engineered layers of polystyrene insulation with a cement-like mud called a topcoat or basecoat, and which is applied with a trowel). The substrates include previously painted, primed, undercoated, worn, or weathered substrates.

The coating composition can be applied to the materials by a variety of techniques well known in the art such as, for example, curtain coating, brush, rollers, mops, air-assisted or airless spray, electrostatic spray, and the like. Paints and clear-coats may or may not partially penetrate, i.e., partially impregnate the substrate upon coating. In an embodiment, a paint composition does not substantially penetrate or impregnate the substrate. In another embodiment, a clear-coat composition does not substantially penetrate or impregnate the substrate. Stains are generally designed to partially or fully impregnate the substrate upon coating. In embodiment, the substrate is fully impregnated by the stain composition, such that the film formed conforms to the interior of the coated substrate, and may be continuous or discontinuous.

Hardening can be by drying, for example storage under atmospheric conditions at room temperature. Drying can also include solvent wicking, for example by the substrate itself (e.g., wood or paper). Heat can be used as an aid to drying. Curing can be used to further harden the film. Curing may be carried out before drying, during drying, or after drying, or any combination thereof.

According to another embodiment, a substrate coated with a dried coating is provided, wherein the dried coating, substrate, or combination thereof comprises the polymer binder in the form of a film comprising the reaction product of polyhydroxy ketal adduct I. The film comprising the reaction product of polyhydroxy ketal adduct I can be a paint, a stain, or a clear-coat. The dried coating comprising the reaction product of can be disposed on a surface of the substrate, in the form of a film that can partially or completely cover the surface. The coating can be disposed directly on the surface, or one or more intermediate layers (e.g., a primer) can be present between the coating and the surface of the substrate. In addition, or alternatively, as described above, the coating can be partially or fully impregnated into the substrate and conform to interior surfaces of the substrate.

The following examples, which are meant to be exemplary, not limiting, illustrate compositions and methods of manufacturing of some of the various embodiments described herein.

EXAMPLES

Example 1. Synthesis of Levulinic Acid-1,4-Butanediol-Levulinic Acid (LA-BDO-LA) with Camphor Sulfonic Acid Catalyst Levulinic acid (268.3 g, 2.3 mol), 1,4-butane-diol (99.3 g, 1.1 mol), and camphor sulfonic acid (73 mg, 200 ppm) were added to an empty 500 mL, 3-neck round bottom flask equipped with a magnetic stir-bar, Dean-Stark trap and overhead condenser, a thermocouple, and a nitrogen inlet. The contents were heated with a heating mantle for 6 hours at 140 to 180° C. A volatile condensate was collected in the Dean Stark trap.

A sample of the condensate was evaluated for the presence of tetrahydrofuran (THF). The condensate was measured to contain 1.8 wt % THF, which correlates to less than 1% yield loss of 1,4-BDO to THF during the esterification reaction.

The product of the reaction crystallized upon cooling. The crystals were washed with water, and a sample of the white solid was analyzed by GC-FID and the composition was found to include 0.13% un-reacted 1,4-BDO, 0.65% un-reacted levulinic acid, 1.1% LA-BDO-OH, 97.9% LA-BDO-LA product, and 0.2% unknown higher molecular weight species. The yield was 220.7 grams.

Example 2: Synthesis of Polyhydroxy Ketal Ester Adduct Ie

Synthesis of the polyhydroxy ketal diester adduct Ie, wherein G is 1,4-butylene, and polyol V is glycerol, was carried out as in Scheme 1.

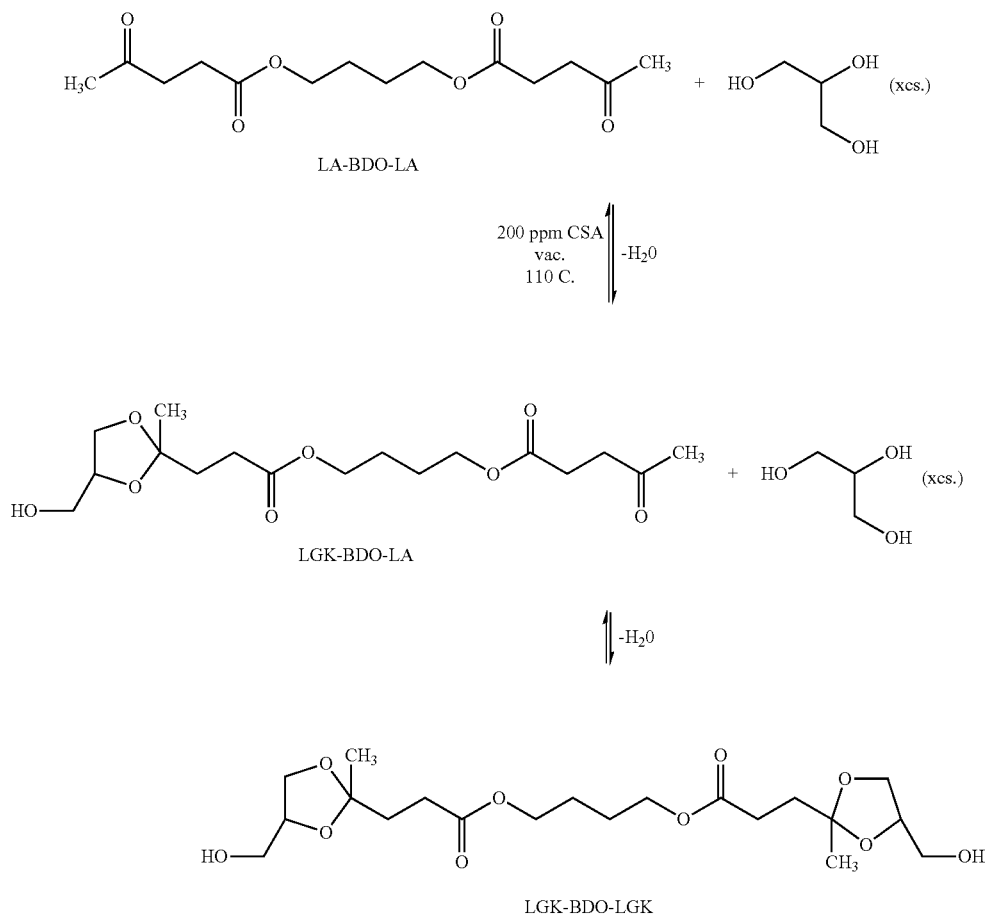

The LA-BDO-LA product from Example 1 (57.6 g, 0.2 mol), glycerol (73.8 g, 0.8 mol), and camphor sulfonic acid (7.5 mg, 50 ppm) were added to an empty 250 mL, 3-neck round bottom flask equipped with a magnetic stir-bar, Dean-Stark trap with an overhead condenser, a thermocouple, and a glass stopper. The contents were heated with a heating mantle for 1 h at 110° C. under 30 Torr vacuum. Volatile condensate was collected in the Dean Stark trap.

After 1 hour, a sample was removed from the reactor and analyzed by GC-FID, the results of which are shown in Table 1.

TABLE 1

| Retention | Identity | Area % |
|---|---|---|
| 7.6 | BDO | 0.20 |
| 8.9 | Glycerol | 23.80 |
| 12.3 | LA-BDO | 1.22 |
| 14.8-15.0 | LGK-BDO | 19.07 |
| 15.4 | LA-BDO-LA | 4.69 |

TABLE 1-continued

| Retention | Identity | Area % |
|---|---|---|
| 16.2 | LGK-BDO-LA | 1.39 |
| 17.1 | LGK-BDO-LGK | 28.27 |
| 15.5-17.7 | Higher MW | 15.4 |
| | Total: | 94.06 |

After cooling, the glycerol phase-separated from the reaction mixture. The excess glycerol was removed from the ketalization by simple decanting or centrifugation. The ketal-adduct diol was analyzed by proton NMR and the conversion of ketone groups to total ketal groups was measured to be 81 wt %, which corresponds to about 74 mol %.

Examples 3 to 5. Synthesis of LA-PDO mono-ol and LGK-PDO Diol

The synthesis of LA-PDO mono-ol and LGK-PDO diol were conducted according to Scheme 2.

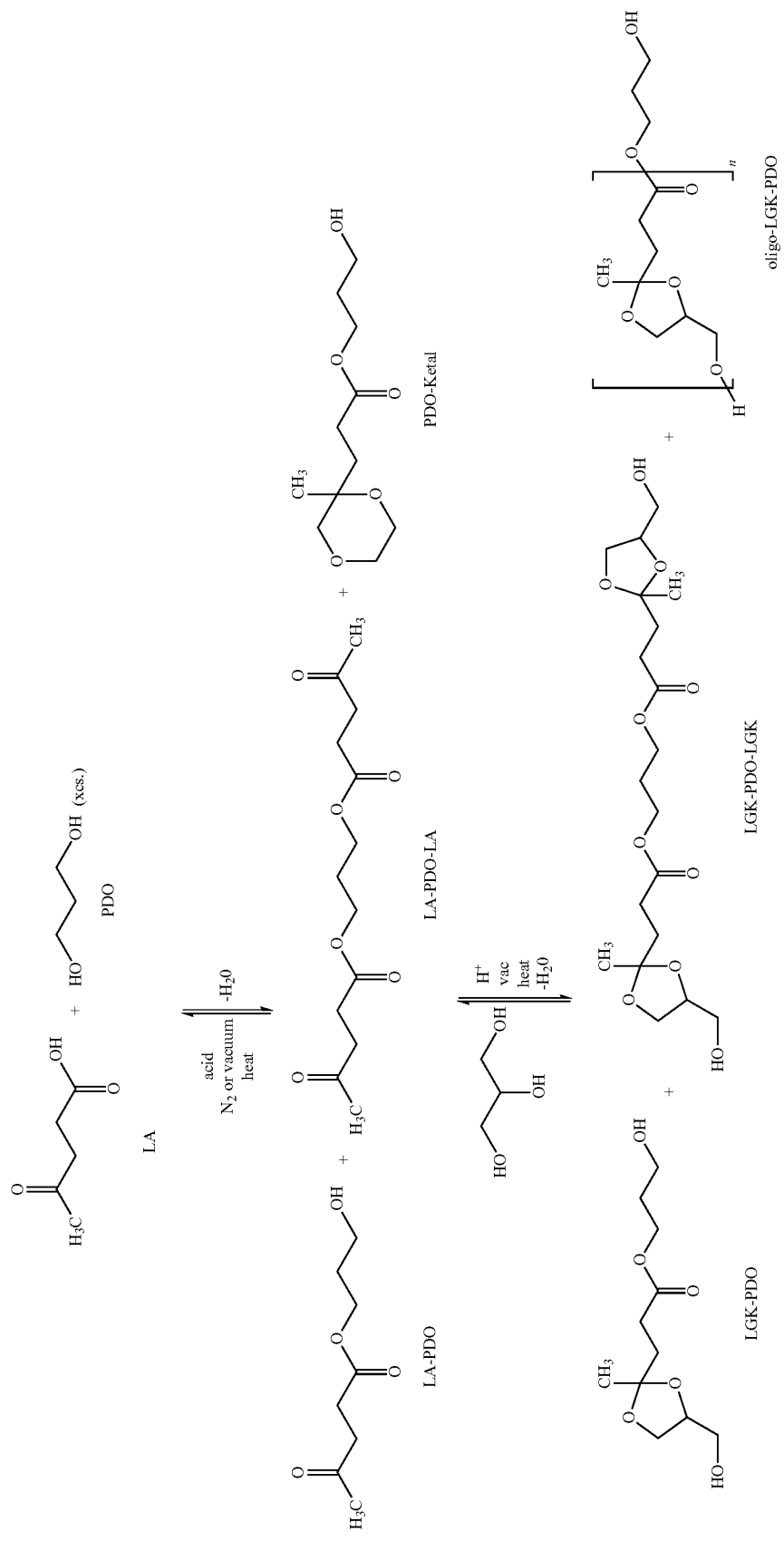

Example 3. Synthesis of LA-PDO

Levulinic acid (200.4 g, 1.7 mol), 1,3-propane-diol (393.4 g, 5.2 mol), and sulfuric acid (8 µL, 25 ppm) were added to an empty 1 L, 3-neck round bottom flask equipped with a magnetic stir-bar, Dean-Stark trap with an overhead condenser, a thermocouple, and a nitrogen inlet. The contents were heated with a heating mantle for approximately 3 hours at 170 to 180° C. Volatile condensate (31.5 mL) was collected in the Dean Stark trap (theoretical collected volume=31 mL).

A sample from the reactor was analyzed by GC-FID, the results of which are shown in Table 2.

TABLE 2

| Retention | Identity | Area % |
|---|---|---|
| 6.4 | 1,3-PDO | 46.1 |
| 9.4 | Levulinic Acid | 0.008 |
| 10.1 | Unidentified Impurity 1 | 0.1 |
| 11.7 | LA-PDO product | 40.0 |
| 13.8 | PDO-ketal | 5.3 |
| 14.9 | LA-PDO-LA | 4.1 |
| 16.6 | Unidentified Impurity 2 | 1.0 |
| 16.6-19.4 | Higher MW impurities | 0.2 |

This process was found to be selective for the synthesis of LA-PDO in high yield. The weight of the final crude reaction mixture was 562 g. The reaction mixture was split into 2 portions for use in Examples 4 and 5.

Example 4. Synthesis of LGK-PDO

The LA-PDO crude product from Example 3 (280 g, 0.64 mol of LA-PDO) and glycerol (29.8 g, 0.32 mol) were added to an empty 500 mL, 3-neck round bottom flask equipped with a magnetic stir-bar, Dean-Stark trap and overhead condenser, a thermocouple, and a glass stopper. The contents were heated with a heating mantle for 12.5 h at 110 to 130° C. under 20 Torr vacuum. Volatile condensate (48.3 g) was collected in the Dean Stark trap.

After 12.5 h, a sample was removed from the reactor and analyzed by GC-FID the results of which are shown in Table 3.

TABLE 3

| Identity | GC Area % |
|---|---|
| 1,3-PDO | 26.9 |
| Glycerol | 0.4 |
| Levulinic Acid | 0.04 |
| Unidentified Impurity 1 | 0.1 |
| LA-PDO | 8.0 |
| PDO-ketal | 30.0 |
| LGK-PDO | 22.2 |
| LA-PDO-LA | 0.2 |
| LGK-PDO-LGK | 1.2 |
| oligo-LGK-PDO | 6.8 |

The reaction was cooled and neutralized with solid dibasic sodium phosphate. The reaction mixture was filtered, and the excess 1,3-propane diol was removed by vacuum distillation. The composition of the final product was analyzed by GC-FID, the results of which are shown in Table 4. The product was a dark yellow, viscous liquid.

TABLE 4

| Identity | Area % |
|---|---|
| 1,3-PDO | 3.7 |
| Glycerol | 0.02 |
| Levulinic Acid | non-detect |
| Unidentified Impurity 1 | 0.1 |
| LA-PDO | 9.3 |
| PDO-Ketal | 27.2 |
| LGK-PDO | 16.0 |
| LA-PDO-LA | 1.5 |
| LGK-PDO-LGK | 7.9 |
| Oligo-LGK-PDO | 29.7 |

Example 5. Synthesis of LGK-PDO

The LA-PDO crude product from Example 3 (267.7 g, 0.61 mol of LA-PDO) and glycerol (28.4 g, 0.31 mol) were added to an empty 500 mL, 3-neck round bottom flask equipped with a magnetic stir-bar, Dean-Stark trap and overhead condenser, a thermocouple, and a glass stopper. The contents were heated with a heating mantle for 3 h at 117-126° C. under 20 Torr vacuum. Volatile condensate (23.1 g) was collected in the Dean Stark trap.

After 3 h, a sample was removed from the reactor and analyzed by GC-FID, the results of which are shown in Table 5.

TABLE 5

| Identity | GC Area % |
|---|---|
| 1,3-PDO | 35.2 |
| Glycerol | 0.75 |
| Levulinic Acid | 0.01 |
| Unidentified Impurity 1 | 0.08 |
| LA-PDO | 15.8 |
| PDO-ketal | 19.1 |
| LGK-PDO | 19.5 |
| LA-PDO-LA | 0.55 |
| LGK-PDO-LGK | 1.36 |
| oligo-LGK-PDO | 4.84 |

The reaction mixture was cooled and neutralized with solid dibasic sodium phosphate. The reaction mixture was filtered, and the excess 1,3-propane diol was removed by vacuum distillation. The composition of the final product as determined by GC-FID is shown in Table 6. The product was a dark yellow, viscous liquid.

TABLE 6

| Identity | Area % |
|---|---|
| 1,3-PDO | 1.0 |
| Glycerol | 0.06 |
| Levulinic Acid | non-detect |
| Unidentified Impurity 1 | 0.01 |
| LA-PDO | 13.2 |
| PDO-Ketal | 23.3 |
| LGK-PDO | 29.9 |
| LA-PDO-LA | 2.3 |
| LGK-PDO-LGK | 4.2 |
| Oligo-LGK-PDO | 22.1 |

Example 6

Example 3 was repeated in a 2 L reaction kettle with the exception that camphor sulfonic acid was used as the esterification catalyst. The reaction was stopped after 4 h and 40 min at a temperature of 150 to 160° C. 56.5 g of volatiles were collected during the reaction. A sample from the reactor was analyzed by GC-FID, the results of which are shown in Table 7.

TABLE 7

| Identity | Area % |
| --- | --- |
| 1,3-PDO | 45.4 |
| Levulinic Acid | 0.004 |
| Unidentified Impurity 1 | 0.5 |
| LA-PDO | 43.3 |
| PDO-Ketal | 3.7 |
| LA-PDO-LA | 5.4 |
| Unidentified Impurity 2 | 0.8 |
| Higher MW impurities | 0.1 |

Into this flask, glycerol (160.73 g, 1.7 moles) was added and the reaction was commenced by heating to 110° C. under a vacuum of 20 torr. The reaction was stopped by ceasing the heating after approximately 4 h, at which time TABLE 8-continued

| Identity | Area % |
| --- | --- |
| Unidentified Impurity 1 | 0.6 |
| LA-PDO | 19.5 |
| PDO-Ketal | 5.2 |
| LGK-PDO | 20.0 |
| LA-PDO-LA | 1.3 |
| LGK-PDO-LGK | 0.7 |
| Oligo-LGK-PDO | 2.7 |

This crude reaction mixture shows higher selectivity toward making the desired LGK-PDO diol product relative to Examples 4 or 5, which provided more of the PDO-Ketal mono-functional alcohol product.

Example 7: Synthesis of LGK-DEG-LGK Diol

Synthesis of the polyhydroxy ketal diester adduct I, wherein G is derived from diethylene glycol and polyol V is glycerol, was carried out as in Scheme 3.

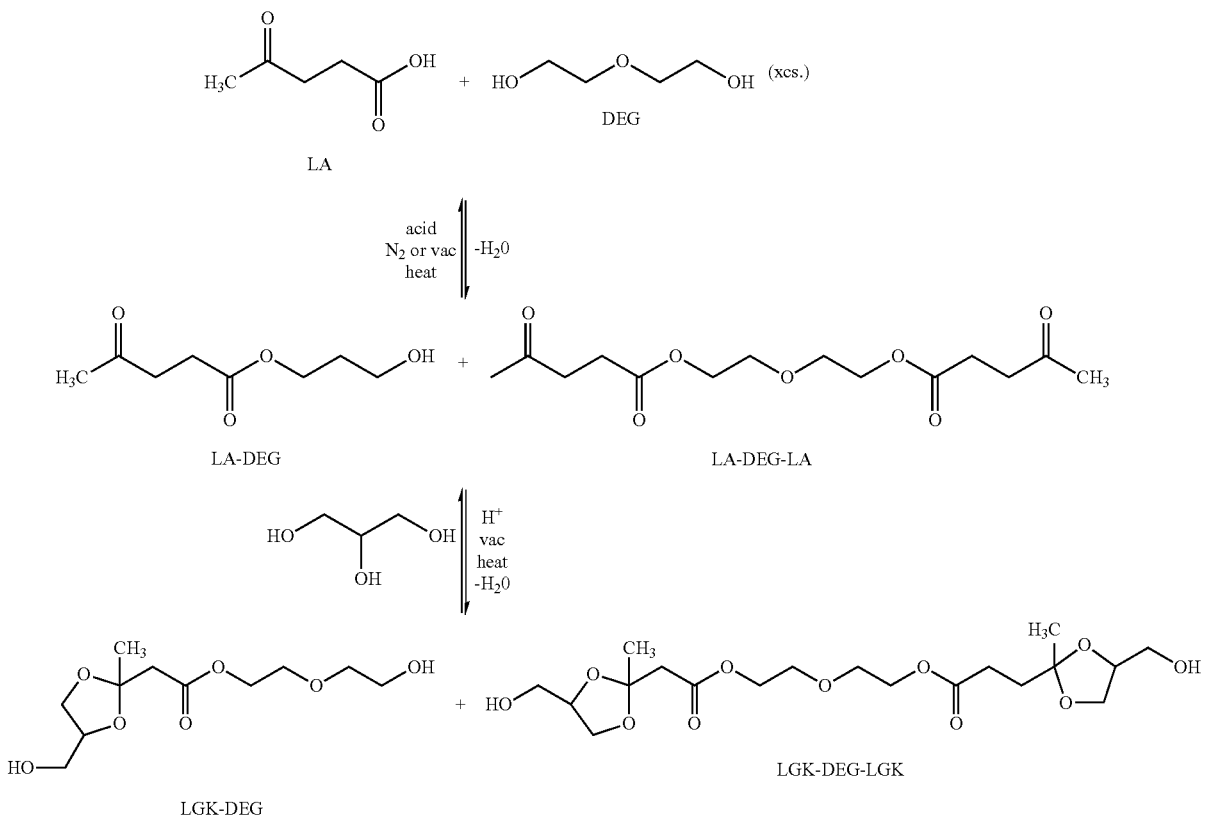

43.4 g of volatile distillate was collected. A sample of the reaction mixture was analyzed by GC-FID, the results of which are shown in Table 8.

TABLE 8

| Identity | Area % |
| --- | --- |
| 1,3-PDO | 41.2 |
| Glycerol | 2.5 |
| Levulinic Acid | 0.01 |

Levulinic acid (151 g, 1.3 mol), diethylene glycol (412.4 g, 3.9 mol), and camphor sulfonic acid (0.114 g) were added to an empty 1 L, 3-neck round bottom flask equipped with a magnetic stir-bar, Dean-Stark trap with overhead condenser, a thermocouple, and a nitrogen inlet. The contents were heated for approximately 3.5 h at 170° C. under nitrogen sweep. The contents were heated an additional 1.5 h at 190° C. Volatile condensate (23 mL) was collected in the Dean Stark trap (theoretical=23 mL).

A sample of the reactor was analyzed by GC-FID and the composition was found to be as shown in Table 9.

TABLE 9

| Identity | Area % (GC-FID) |
| --- | --- |
| Diethylene glycol | 47.9 |
| Lev. Acid | Non/detect |
| Unidentified Impurities | 2.3 |
| LA-DEG product | 43.3 |
| LA-DEG-LA | 6.5 |

This process was found to be selective for the synthesis of LA-DEG in high yield.

Glycerol (107.5 g, 1.17 mol) was added to the LA-DEG crude reaction mixture. The contents were heated with a heating mantle for 2 h at 90° C. under 10-35 Torr vacuum. After 2 h of reaction, 52 mg of camphor sulfonic acid catalyst was charged into the reaction. The contents were heated an additional 1.5 h at 90° C. under 10 Torr vacuum. Volatile condensate (15-16 mL) was collected in the Dean Stark trap. A sample was analyzed by GC-FID, results being shown in Table 10.

TABLE 10

| Identity | Area % (GC-FID) |
| --- | --- |
| Diethylene glycol | 48.4 |
| Lev. Acid | Non-detect |
| Glycerol | Non-detect |
| LA-DEG | 19.1 |
| LGK-DEG Product | 23.5 |
| LA-DEG-LA | 1.2 |
| Impurities of Unknown Composition | 7.8 |

The contents were heated for an additional 1 h at 100-110° C. under 10 Torr vacuum. The contents were cooled and neutralized with dibasic sodium phosphate, stirred at 70° C. for 1 h, and filtered. The reaction mixture was distilled on a wiped film evaporator (WFE) at 150° C. and 0.5 Torr. The split ratio of overheads to bottoms was roughly 60:40. The bottoms from the first WFE purification were distilled by WFE at 150° C. and 0.1-0.2 Torr. The split ratio of overheads to bottoms was roughly 60:40 for 35 min and changed to 90:10 for 45 min. A sample was analyzed by GC-FID. The composition was found to be as shown in Table 11.

TABLE 11

| Identity | Area % (GC-FID) |
| --- | --- |
| Diethylene glycol | 1.3 |
| Cyclic impurities | 1.3 |
| Glycerol | Non-detect |
| LA-DEG | 3.9 |
| LGK-DEG Product | 82.1 |
| LA-DEG-LA | 2.9 |
| Impurities of Unknown Composition | 8.5 |

The product was a colorless, viscous liquid. The YI was 1.4, the viscosity was 330 cP at 25 C. It displayed a ketone/ketal ratio of 0.29 by 1H NMR.

Example 8. Polyurethane Foam

A rigid polyurethane foam was made with the product from Example 7. The formulation for the foam was as shown in Table 12.

TABLE 12

| A-side | EW | Grams | ml |
| --- | --- | --- | --- |
| Mondur ® MRS (Bayer-PMDI) | 133 | 23.75 | 19.47 |

| B-side | EW | Parts | Grams |
| --- | --- | --- | --- |
| Example 7 | 139 | 100 | 19.21 |
| Water | 9 | 0.8 | 0.15 |
| L6900 (Momentive) |  | 2 | 0.38 |
| Polycat 8 ® (Air Products) |  | 1 | 0.19 |
| Polycat 5 ® (Air Products) |  | 0.3 | 0.06 |
| HFC-245FA (DuPont) |  | 30 | 5.76 |

The B-side was mixed at room temperature for 1 min to ensure the mixture was homogeneous. The polymeric isocyanate, Mondur® MRS, was added via syringe. The reaction mixture was stirred by a high-speed mixer at 1800 rpm for 10 seconds. The impeller was removed, and the foam was allowed to rise and harden. The foam was aged for 24 h at room temperature. The foam was cut into squares with an electric bandsaw. The samples were aged in an oven at 25° C. and 50% relative humidity for 48 h. The density of the foam was 38.6 kg/m$^3$. The samples were analyzed for compressive strength on an MTS Instron Instrument according to ASTM D1621. The compressive strength was found to be 228.2 kPa. The foams were quite rigid in nature.

Example 9. LA-BDO-LA

A pure sample of LA-BDO-LA was prepared from a pure (>95%) levulinic acid and excess 1,4-butanediol. After crystallization, the isolated LA-BDO-LA was >98.5% pure, as determined by GC-FID (peak area).

Example 10

To a 250 mL round bottom flask equipped with a magnetic stir bar was charged 60.10 g of the LA-BDO-LA prepared in Example 9, 96.48 g glycerol, and 33.3 mg (210 ppm) camphor sulfonic acid. The reaction flask was assembled on a short path distillation apparatus and evacuated to a pressure of 150 Torr. The reaction was then heated to 100 C before further reducing the pressure down to 10 Torr. The reaction was held between 10 and 13 Torr and 114-118° C. for 10.5 hours, at which point the reaction was cooled to room temperature under vacuum. The final isolated product (126.05 g) contained 31.0% LGK-BDO-LGK (structure I), 1.7% LGK-BDO-LA (structure II), and 32.2% unreacted glycerol, as determined by GC-FID and GC-MS.

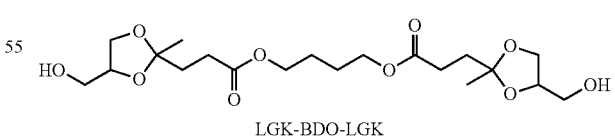

LGK-BDO-LGK

Structure I.

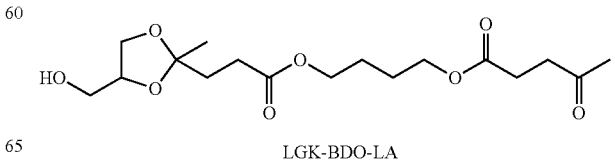

LGK-BDO-LA

Structure II.

Example 11. LA-BDO-LA and Sulfuric Acid

To a round bottom flask with stirring is added 60.10 g of the LA-BDO-LA prepared in Example 9, 96.48 g glycerol, and 32.9 mg (210 ppm) concentrated sulfuric acid (Dow Chemical Company). The reaction flask is assembled on a short path distillation apparatus and evacuated to a pressure of 150 Torr. The reaction is next heated to 100° C. before further reducing the pressure down to 10 Torr. The reaction is maintained between 10 and 13 Torr and 114-118° C. for 10.5 hours, at which point the reaction can be cooled to room temperature under vacuum.

Example 12. Preparation with Amberlyst 35 Catalyst

To a round bottom flask with stirring is added 60.10 g of the LA-BDO-LA prepared in Example 9, 96.48 g glycerol, and 32.9 mg (210 ppm) Amberlyst 35 catalyst (Dow Chemical Company). The reaction flask is assembled on a short path distillation apparatus and evacuated to a pressure of 150 Torr. The reaction is next heated to 100° C. before further reducing the pressure down to 10 Torr. The reaction is maintained between 10 and 13 Torr and 114-118° C. for 10.5 hours, at which point the reaction can be cooled to room temperature under vacuum.

Example 13

The crude reaction mixture prepared in Example 11 is purified on a wiped film evaporator (WFE). The WFE is first equilibrated around 200 mTorr and between 98 and 104° C. before the crude reaction mixture is added at an approximate rate of 1 g/min. A low boiling and high boiling fraction are obtained, with the desired LGK-BDO-LGK in the high boiling fraction, as determined by GC-FID and $^1$H NMR. From the $^1$H NMR spectrum, 92% of the ketone groups of the original LA-BDO-LA are ketalized as determined by integration of the signal corresponding to the protons adjacent to the ketone group appearing at 2.1 ppm relative to that of the protons alpha to the primary hydroxyl of LGK at 3.4 ppm. Including the approximately 5% glycerol observed in the $^1$H NMR spectrum, the average degree of functionality of the reaction mixture is calculated to be 1.9.

Example 14. LA-PDO-LA using AMBERLYST 35 catalyst Prophetic

To a round bottom flask with stirring is added 60.10 g of the LA-PDO-LA prepared in Example 9, 96.48 g glycerol, and 32.9 mg (210 ppm) Amberlyst 35 catalyst (Dow Chemical Company). The reaction flask is assembled on a short path distillation apparatus and evacuated to a pressure of 150 Torr. The reaction is next heated to 100° C. before further reducing the pressure down to 10 Torr. The reaction is maintained between 10 and 13 Torr and 114-118° C. for 10.5 hours, at which point the reaction can be cooled to room temperature under vacuum.

Example 15

The purification of the crude reaction mixture of Example 14 is accomplished on a wiped film evaporator (WFE). The WFE is first equilibrated near 200 mTorr and 100° C. before the crude reaction mixture is added at an approximate rate of 1 g/min. A low boiling and high boiling fraction will be obtained, with the desired LGK-PDO-LGK in the high boiling fraction. The resulting high boiling fraction is expected to contain no more than 5% glycerol and display an average functionality between 1.85 and 2.05.

Example 16. LA-DEG-LA and Sulfuric Acid. Prophetic

To a round bottom flask with stirring is added 60.10 g of the LA-DEG-LA prepared in Example 9, 96.48 g glycerol, and 32.9 mg (210 ppm) concentrated sulfuric acid (Dow Chemical Company). The reaction flask is assembled on a short path distillation apparatus and evacuated to a pressure of 150 Torr. The reaction is next heated to 100° C. before further reducing the pressure down to 10 Torr. The reaction is maintained between 10 and 13 Torr and 114-118° C. for 10.5 hours, at which point the reaction can be cooled to room temperature under vacuum.

Example 17. LA-DEG-LA and Amberlyst 35 Catalyst Prophetic

To a round bottom flask with stirring is added 60.10 g of the LA-DEG-LA prepared in Example 7, 96.48 g glycerol, and 32.9 mg (210 ppm) Amberlyst 35 catalyst (Dow Chemical Company). The reaction flask is assembled on a short path distillation apparatus and evacuated to a pressure of 150 Torr. The reaction is next heated to 100° C. before further reducing the pressure down to 10 Torr. The reaction is maintained between 10 and 13 Torr and 114-118° C. for 10.5 hours, at which point the reaction can be cooled to room temperature under vacuum.

Example 18

The purification of the crude reaction mixtures of Examples 16 or 17 are accomplished on a wiped film evaporator (WFE). The WFE is first equilibrated near 200 mTorr and 100° C. before the crude reaction mixture is added at an approximate rate of 1 g/min. A low boiling and high boiling fraction will be obtained, with the desired LGK-DEG-LGK in the high boiling fraction.

As used herein, the singular forms "a," "an," and "the" are intended to include the plural forms as well, unless the context clearly indicates otherwise. The endpoints of all ranges directed to the same component or property are inclusive of the endpoint and independently combinable, except when the modifier "between" is used. The modifier "about" used in connection with a quantity is inclusive of the stated value and has the meaning dictated by the context (e.g., includes the degree of error associated with measurement of the particular quantity). A "combination" is inclusive of blends, mixtures, alloys, reaction products, and the like.

In general, the compositions or methods can alternatively comprise, consist of, or consist essentially of, any appropriate components or steps disclosed. The invention can additionally, or alternatively, be formulated so as to be devoid, or substantially free, of any components, materials, ingredients, adjuvants, or species, or steps used in the prior art compositions or that are otherwise not necessary to the achievement of the function and/or objectives of the present claims.

Unless otherwise defined, all terms (including technical and scientific terms) used have the same meaning as commonly understood by one of ordinary skill in the art to which this invention belongs. Compounds are described using standard nomenclature. Any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

"Alkyl" means a straight or branched chain saturated aliphatic hydrocarbon having the specified number of carbon atoms and a valence of at least 1. "Alkylene" means a straight or branched divalent aliphatic hydrocarbon group having the specified number of carbon atoms and a valence of at least 2 as determined by the value of t or p+q. "Aryl" means a cyclic moiety in which all ring members are carbon and a ring is aromatic, and having a valence of at least 1. More than one ring can be present, and any additional rings can be independently aromatic, saturated or partially unsaturated, and can be fused, pendant, spirocyclic or a combination thereof.

"Hydrocarbylene" means a group having the specified number of carbon atoms and the appropriate valence in view of the number of substitutions shown in the structure. Hydrocarbylene groups contain at least carbon and hydrogen, and can optionally contain 1 or more (e.g., 1-8) heteroatoms selected from N, O, S, Si, P, or a combination thereof. Hydrocarbylene groups can be unsubstituted or substituted with one or more substituent groups up to the valence allowed by the hydrocarbylene group independently selected from a C1-30 alkyl, C2-30 alkenyl, C2-30 alkynyl, C6-30 aryl, C7-30 arylalkyl, C1-12 alkoxy, C1-30 heteroalkyl, C3-30 heteroarylalkyl, C3-30 cycloalkyl, C3-15 cycloalkenyl, C6-30 cycloalkynyl, C2-30 heterocycloalkyl, halogen (F, Cl, Br, or I), hydroxy, nitro, cyano, amino, azido, amidino, hydrazino, hydrazono, carbonyl, carbamyl, thiol, carboxy (C1-6alkyl) ester, carboxylic acid, carboxylic acid salt, sulfonic acid or a salt thereof, and phosphoric acid or a salt thereof.

While stereochemistry of the various compounds is not explicitly shown, it is to be understood that this disclosure encompasses all isomers.

All cited patents, patent applications, and other references are incorporated by reference in their entirety.

While the invention has been described with reference to exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising
essentially no transition metal; and
a polyhydroxy ketal adduct I $$\left[\left[\begin{array}{c}R^2\\ \phantom{X}\\ \phantom{X}\end{array}\right]_a \cdots O \cdots \left[G\right] \cdots O \cdots \left[\begin{array}{c}R^2\\ \phantom{X}\\ \phantom{X}\end{array}\right]_a\right]_{q-n} \quad\quad I$$

wherein
G is a $C_{2-8}$ alkylene, $C_{2-8}$ alkenylene, $C_{6-12}$ arylene, or a $(R^{12}O)_u R^{12}$— group having 4 to 16 carbon atoms, wherein each $R^{12}$ is independently ethylene, 1,3-propylene, or 1,2-propylene, and u=1-7,
each $R^2$ is independently $C_{1-3}$ alkyl,
each $R^3$, $R^4$, and $R^6$ is independently hydrogen or $C_{1-3}$ alkyl,
each $R^7$ is independently $C_{1-6}$ alkylene,
each a is independently=0-3,
each b is independently=0-1,
each m is independently=1-30,
p=0-9,
q−n=1-8, and
n=1-10, provided that p+n≥2, and q≥n.

2. The composition of claim 1, wherein
p=0-7,
q−n=1-6, and
n=1-8, provided that p+n≥2, and q≥n.

3. The composition of claim 2, wherein
G is a $C_{2-6}$ alkylene or —$(CH_2CH_2OCH_2CH_2)$—,
each m=1 to 5, and
either n=1 and p=1, or n=2 and p=0.

4. The composition of claim 1, wherein
G is $C_{2-8}$ alkylene or a —$(R^{12}O)_u R^{12}$— group having 4 to 9 carbon atoms wherein each $R^{12}$ is independently ethylene, 1,3-propylene, or 1,2-propylene, and u=1-2,
each a is independently 1-2,
each b is independently=0-1, and
each m is independently=1-20.

5. The composition of claim 1, wherein
G is $C_{2-6}$ alkylene or a —$(R^{12}O)_u R^{12}$— group having 4 to 12 carbon atoms, wherein $R^{12}$ is ethylene, or 1,3-propylene and u=1-5,
each m is independently=1-30,
p=0-3, and
n=1-4, provided that n+p=2-4.

6. The composition of claim 5, wherein
G is $C_{2-6}$ alkylene or a —$(R^{12}O)_u R^{12}$— group having 4 to 10 carbon atoms wherein $R^{12}$ is ethylene and u=1-4,
each m is independently 1-20,
p=0-2, and
n=1-3, provided that n+p=2-3.

7. The composition of claim 6, wherein
G is $C_{2-6}$ alkylene or a —$(R^{12}O)_u R^{12}$— group having 4 to 10 carbon atoms wherein $R^{12}$ is ethylene and u=1-4,
each m is independently=1-10,
p=0, and
n=1-3.

8. A polymer composition comprising
a polymer; and
the composition of claim 1.

9. A polyester comprising ester units derived from polymerization of a carboxylic diacid and the composition of claim 1.

10. A composition comprising
essentially no transition metal; and
a polyhydroxy ketal adduct I of the formula $$\text{Ie}$$

-continued

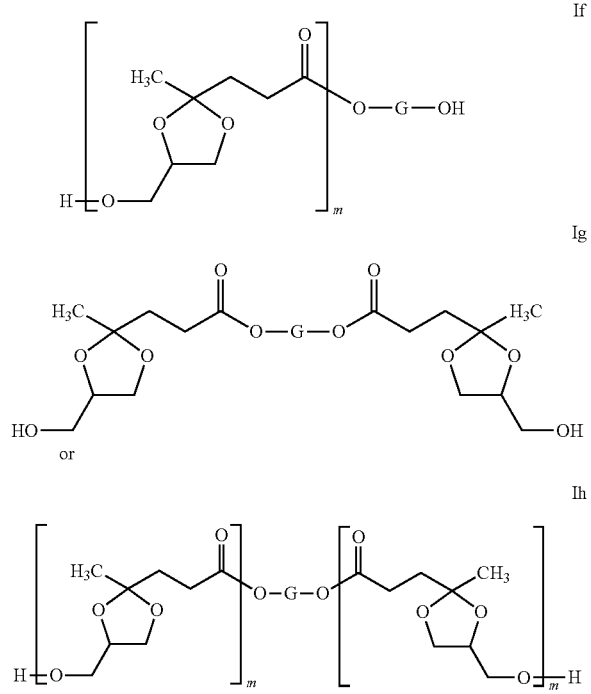

wherein
G is a $C_{2-6}$ alkylene or $-(CH_2CH_2OCH_2CH_2)-$, and each m is independently=1 to 50;
wherein the composition further comprises
a ketocarboxylic ester (IV),

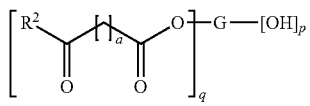

a hydroxy ketoester (VII),

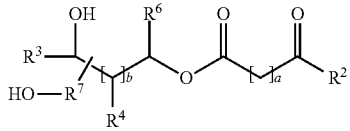

or a hydroxy ketal ester (VIII),

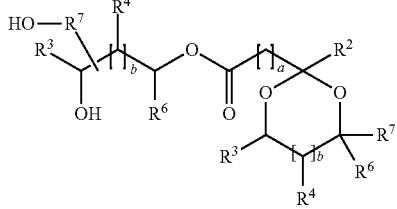

or a combination comprising at least one of the foregoing, wherein
each $R^2$ is independently $C_{1-6}$ alkyl,
each $R^3$, $R^4$, and $R^6$ is each independently hydrogen, $C_{1-6}$ alkyl, $-OR^8$ wherein $R^8$ is $C_{1-4}$ alkyl, or $-C(O)R^9$ wherein $R^9$ is $C_{1-4}$ alkyl,
each $R^7$ is independently $C_{1-6}$ alkylene, or $C_{1-6}$ alkylene substituted with one $-OR^8$ group wherein $R^8$ is $C_{1-3}$ alkyl, or $-C(O)R^9$ wherein $R^9$ is $C_{1-2}$ alkyl,
each a is independently=0-3,
each b is independently=0-1,
p=0-11, and
q=1-12, provided p+q≥2 and q+p is the valence of G.

11. The composition of claim 10, wherein at least one of ketocarboxylic ester IV, hydroxy ketoester VII, or hydroxy ketal ester VIII is present in an amount of greater than zero to 10 wt %, based on a total weight of the composition.

* * * * *